United States Patent
Kumar et al.

(10) Patent No.: US 9,867,671 B2
(45) Date of Patent: Jan. 16, 2018

(54) MULTI-USER MEDICAL ROBOTIC SYSTEM FOR COLLABORATION OR TRAINING IN MINIMALLY INVASIVE SURGICAL PROCEDURES

(71) Applicant: Intuitive Surgical Operations, Inc., Sunnyvale, CA (US)

(72) Inventors: Rajesh Kumar, Sunnyvale, CA (US); Brian D. Hoffman, Mountain View, CA (US); Giuseppe Maria Prisco, Calci (IT); David Q. Larkin, Menlo Park, CA (US); William C. Nowlin, Los Altos Hills, CA (US); Frederic H. Moll, San Francisco, CA (US); Stephen J. Blumenkranz, Los Altos Hills, CA (US); Gunter D. Niemeyer, Pasadena, CA (US); J. Kenneth Salisbury, Jr., Mountain View, CA (US); Yulun Wang, Goleta, CA (US); Modjtaba Ghodoussi, Santa Barbara, CA (US); Darrin R. Uecker, San Mateo, CA (US); James W. Wright, Santa Barbara, CA (US); Amante A. Mangaser, Goleta, CA (US); Ranjan Mukherjee, East Lansing, MI (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/607,676

(22) Filed: May 29, 2017

(65) Prior Publication Data
US 2017/0258537 A1  Sep. 14, 2017

Related U.S. Application Data

(60) Continuation of application No. 15/006,555, filed on Jan. 26, 2016, now Pat. No. 9,666,101, which is a
(Continued)

(51) Int. Cl.
*A61B 34/37* (2016.01)
*A61B 90/00* (2016.01)
(Continued)

(52) U.S. Cl.
CPC ............... *A61B 34/37* (2016.02); *A61B 34/70* (2016.02); *A61B 90/37* (2016.02);
(Continued)

(58) Field of Classification Search
USPC ................................................. 700/245–264
See application file for complete search history.

(56) References Cited

U.S. PATENT DOCUMENTS

| 977,825 A | 12/1910 | George |
| 1,327,577 A | 1/1920 | Turner |

(Continued)

FOREIGN PATENT DOCUMENTS

| DE | 9204118 U1 | 5/1992 |
| DE | 4310842 C2 | 1/1996 |

(Continued)

OTHER PUBLICATIONS

Abstract of a presentation "3-D Vision Technology Applied to Advanced Minimally Invasive Surgery Systems," (Session 15/3) given at the 3rd World Congress of Endoscopic Surgery in Bordeaux, Jun. 18-20, 1992, 1 page.
(Continued)

*Primary Examiner* — Jonathan L Sample

(57) ABSTRACT

A multi-user medical robotic system for collaboration or training in minimally invasive surgical procedures includes first and second master input devices, a first slave robotic mechanism, and at least one processor configured to generate a first slave command for the first slave robotic mechanism by switchably using one or both of a first command indicative of manipulation of the first master input device by
(Continued)

a first user and a second command indicative of manipulation of the second master input device by a second user. To facilitate the collaboration or training, both first and second users communicate with each other through an audio system and see the minimally invasive surgery site on first and second displays respectively viewable by the first and second users.

6 Claims, 10 Drawing Sheets

Related U.S. Application Data division of application No. 13/965,581, filed on Aug. 13, 2013, now Pat. No. 9,271,798, which is a division of application No. 11/319,012, filed on Dec. 27, 2005, now Pat. No. 8,527,094, and a continuation-in-part of application No. 11/025,766, filed on Dec. 28, 2004, now abandoned, which is a continuation of application No. 10/214,286, filed on Aug. 6, 2002, now Pat. No. 6,858,003, which is a division of application No. 09/436,982, filed on Nov. 9, 1999, now Pat. No. 6,468,265, and a continuation-in-part of application No. 09/433,120, filed on Nov. 3, 1999, now Pat. No. 6,659,939, which is a continuation-in-part of application No. 09/399,457, filed on Sep. 17, 1999, now abandoned, which is a continuation-in-part of application No. 09/374,643, filed on Aug. 16, 1999, now abandoned, said application No. 11/319,012 is a continuation-in-part of application No. 10/948,853, filed on Sep. 23, 2004, now Pat. No. 7,413,565, which is a division of application No. 10/246,236, filed on Sep. 17, 2002, now Pat. No. 6,951,535, which is a continuation-in-part of application No. 10/051,796, filed on Jan. 16, 2002, now Pat. No. 6,852,107.

(60) Provisional application No. 60/725,770, filed on Oct. 12, 2005, provisional application No. 60/109,303, filed on Nov. 20, 1998, provisional application No. 60/109,301, filed on Nov. 20, 1998, provisional application No. 60/150,145, filed on Aug. 20, 1999, provisional application No. 60/116,891, filed on Jan. 22, 1999, provisional application No. 60/116,842, filed on Jan. 22, 1999, provisional application No. 60/109,359, filed on Nov. 20, 1998.

(51) Int. Cl.
*A61B 34/00* (2016.01)
*G09B 23/28* (2006.01)
*A61B 1/00* (2006.01)
*A61B 17/00* (2006.01)

(52) U.S. Cl.
CPC ......... *A61B 1/00193* (2013.01); *A61B 90/361* (2016.02); *A61B 2017/00017* (2013.01); *G09B 23/28* (2013.01)

(56) References Cited

U.S. PATENT DOCUMENTS

| | | |
|---|---|---|
| 3,171,549 A | 3/1965 | Orloff |
| 3,280,991 A | 10/1966 | Melton et al. |
| 3,497,668 A | 2/1970 | Hirsch |
| 3,628,535 A | 12/1971 | Ostrowsky et al. |
| 3,698,791 A | 10/1972 | Walchle et al. |
| 3,880,166 A | 4/1975 | Fogarty |
| 3,910,280 A | 10/1975 | Talonn |
| 3,961,921 A | 6/1976 | Heiman et al. |
| 3,993,076 A | 11/1976 | Fogarty |
| 4,041,942 A | 8/1977 | Dougan et al. |
| 4,058,001 A | 11/1977 | Waxman |
| 4,062,455 A | 12/1977 | Flatau |
| 4,078,568 A | 3/1978 | Etes et al. |
| 4,101,961 A | 7/1978 | Fletcher et al. |
| 4,128,880 A | 12/1978 | Cray, Jr. |
| 4,182,311 A | 1/1980 | Seppi et al. |
| 4,221,997 A | 9/1980 | Flemming |
| 4,337,045 A | 6/1982 | Jones et al. |
| 4,349,837 A | 9/1982 | Hinds |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,511,305 A | 4/1985 | Kawai et al. |
| 4,517,963 A | 5/1985 | Michel |
| 4,523,884 A | 6/1985 | Clement et al. |
| 4,586,398 A | 5/1986 | Yindra |
| 4,598,725 A | 7/1986 | Brewer |
| 4,604,016 A | 8/1986 | Joyce |
| 4,614,499 A | 9/1986 | Arseneault et al. |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,635,479 A | 1/1987 | Salisbury, Jr. |
| 4,641,292 A | 2/1987 | Tunnell et al. |
| 4,649,930 A | 3/1987 | Groch et al. |
| 4,655,257 A | 4/1987 | Iwashita |
| 4,655,673 A | 4/1987 | Hawkes |
| 4,672,963 A | 6/1987 | Barken |
| 4,676,243 A | 6/1987 | Clayman |
| 4,728,974 A | 3/1988 | Nio et al. |
| 4,750,636 A | 6/1988 | Wortham |
| 4,762,455 A | 8/1988 | Coughlan et al. |
| 4,764,944 A | 8/1988 | Finlayson |
| 4,791,934 A | 12/1988 | Brunnett |
| 4,791,940 A | 12/1988 | Hirschfeld et al. |
| 4,794,912 A | 1/1989 | Lia |
| 4,799,779 A | 1/1989 | Mesmer |
| 4,800,614 A | 1/1989 | Kopco et al. |
| 4,815,006 A | 3/1989 | Andersson et al. |
| 4,815,450 A | 3/1989 | Patel |
| 4,817,592 A | 4/1989 | Auchinleck et al. |
| 4,819,978 A | 4/1989 | Scheinman et al. |
| 4,826,392 A | 5/1989 | Hayati |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,891,767 A | 1/1990 | Rzasa et al. |
| 4,930,494 A | 6/1990 | Takehana et al. |
| 4,942,538 A | 7/1990 | Yuan et al. |
| 4,942,539 A | 7/1990 | McGee et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,036,463 A | 7/1991 | Abela et al. |
| 5,046,022 A | 9/1991 | Conway et al. |
| 5,046,375 A | 9/1991 | Salisbury, Jr. |
| 5,053,687 A | 10/1991 | Merlet |

(56) References Cited

U.S. PATENT DOCUMENTS

| | | |
|---|---|---|
| 5,053,975 A | 10/1991 | Tsuchihashi et al. |
| 5,056,031 A | 10/1991 | Nakano et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,119,817 A | 6/1992 | Allen |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,319 A | 2/1993 | Kramer |
| 5,184,601 A | 2/1993 | Putman |
| 5,186,232 A | 2/1993 | Zahner |
| 5,187,574 A | 2/1993 | Kosemura et al. |
| 5,193,963 A | 3/1993 | McAffee et al. |
| 5,196,688 A | 3/1993 | Hesse et al. |
| 5,198,894 A | 3/1993 | Hicks |
| 5,201,325 A | 4/1993 | McEwen et al. |
| 5,201,743 A | 4/1993 | Haber et al. |
| 5,204,942 A * | 4/1993 | Otera ............... G05B 19/4182 700/248 |
| 5,210,911 A | 5/1993 | Brown et al. |
| 5,213,141 A | 5/1993 | Dorman |
| 5,217,003 A | 6/1993 | Wilk |
| 5,217,453 A | 6/1993 | Wilk |
| 5,221,283 A | 6/1993 | Chang |
| 5,222,499 A | 6/1993 | Allen et al. |
| 5,228,429 A | 7/1993 | Hatano |
| 5,230,338 A | 7/1993 | Allen et al. |
| 5,230,623 A | 7/1993 | Guthrie et al. |
| 5,231,693 A | 7/1993 | Backes et al. |
| 5,233,516 A | 8/1993 | Le Roux |
| 5,236,432 A | 8/1993 | Matsen, III et al. |
| 5,239,883 A | 8/1993 | Rosheim |
| 5,239,981 A | 8/1993 | Anapliotis |
| 5,240,011 A | 8/1993 | Assa |
| 5,251,127 A | 10/1993 | Raab |
| 5,251,128 A | 10/1993 | Crawford |
| 5,253,289 A | 10/1993 | Tanaka |
| 5,257,999 A | 11/1993 | Slanetz, Jr. |
| 5,271,384 A | 12/1993 | McEwen et al. |
| 5,274,500 A | 12/1993 | Dunn |
| 5,275,608 A | 1/1994 | Forman et al. |
| 5,279,309 A | 1/1994 | Taylor et al. |
| 5,282,806 A | 2/1994 | Haber et al. |
| 5,282,826 A | 2/1994 | Quadri |
| 5,284,130 A | 2/1994 | Ratliff |
| 5,289,273 A | 2/1994 | Lang |
| 5,289,365 A | 2/1994 | Caldwell et al. |
| 5,297,034 A | 3/1994 | Weinstein |
| 5,299,288 A | 3/1994 | Glassman et al. |
| 5,300,926 A | 4/1994 | Stoeckl |
| 5,301,657 A | 4/1994 | Lafferty et al. |
| 5,303,148 A | 4/1994 | Mattson et al. |
| 5,304,149 A | 4/1994 | Morigi |
| 5,304,185 A | 4/1994 | Taylor |
| 5,305,149 A | 4/1994 | Newman et al. |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,321,353 A | 6/1994 | Furness |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,403,332 A | 4/1995 | Christoudias |
| 5,408,409 A | 4/1995 | Glassman et al. |
| 5,410,638 A | 4/1995 | Colgate et al. |
| 5,410,944 A | 5/1995 | Cushman |
| 5,413,092 A | 5/1995 | Williams, III et al. |
| 5,417,210 A | 5/1995 | Funda et al. |
| 5,417,701 A | 5/1995 | Holmes |
| 5,422,521 A | 6/1995 | Neer et al. |
| 5,423,648 A | 6/1995 | Akeel et al. |
| 5,429,142 A | 7/1995 | Szabo et al. |
| 5,431,645 A | 7/1995 | Smith et al. |
| 5,434,457 A | 7/1995 | Josephs et al. |
| 5,441,042 A | 8/1995 | Putman |
| 5,442,728 A | 8/1995 | Kaufman et al. |
| 5,443,484 A | 8/1995 | Kirsch et al. |
| 5,445,166 A | 8/1995 | Taylor |
| 5,451,852 A | 9/1995 | Gusakov |
| 5,451,924 A | 9/1995 | Massimino et al. |
| 5,452,733 A | 9/1995 | Sterman et al. |
| 5,453,686 A | 9/1995 | Anderson |
| 5,454,827 A | 10/1995 | Aust et al. |
| 5,455,766 A | 10/1995 | Scheller et al. |
| 5,458,547 A | 10/1995 | Teraoka et al. |
| 5,458,574 A | 10/1995 | MacHold et al. |
| 5,464,410 A | 11/1995 | Skeens et al. |
| 5,467,223 A | 11/1995 | Cleveland, Jr. |
| 5,474,571 A | 12/1995 | Lang |
| 5,476,010 A | 12/1995 | Fleming et al. |
| 5,478,351 A | 12/1995 | Meade et al. |
| 5,489,292 A | 2/1996 | Tovey et al. |
| 5,490,117 A | 2/1996 | Oda et al. |
| 5,490,843 A | 2/1996 | Hildwein |
| 5,506,912 A | 4/1996 | Nagasaki et al. |
| 5,512,919 A | 4/1996 | Araki |
| 5,514,157 A | 5/1996 | Nicholas et al. |
| 5,515,478 A | 5/1996 | Wang |
| 5,524,180 A | 6/1996 | Wang et al. |
| 5,531,520 A | 7/1996 | Grimson et al. |
| 5,544,654 A | 8/1996 | Murphy et al. |
| 5,553,198 A | 9/1996 | Wang et al. |
| 5,553,609 A * | 9/1996 | Chen ................... G06F 19/322 128/904 |
| 5,562,503 A | 10/1996 | Ellman et al. |
| 5,571,110 A | 11/1996 | Matsen, III |
| 5,572,999 A | 11/1996 | Funda et al. |
| 5,586,564 A | 12/1996 | Barrett et al. |
| 5,588,432 A | 12/1996 | Crowley |
| 5,597,146 A | 1/1997 | Putman |
| 5,608,847 A | 3/1997 | Pryor |
| 5,609,560 A | 3/1997 | Ichikawa et al. |
| 5,613,937 A | 3/1997 | Garrison et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,647,361 A | 7/1997 | Damadian |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,693,071 A | 12/1997 | Gorecki et al. |
| 5,695,500 A | 12/1997 | Taylor et al. |
| 5,696,574 A | 12/1997 | Schwaegerle |
| 5,696,837 A | 12/1997 | Green |
| 5,697,939 A | 12/1997 | Kubota et al. |
| 5,704,791 A | 1/1998 | Gillio |

(56) References Cited

U.S. PATENT DOCUMENTS

| | | |
|---|---|---|
| 5,715,729 A | 2/1998 | Toyama et al. |
| 5,715,836 A | 2/1998 | Kliegis et al. |
| 5,718,038 A | 2/1998 | Takiar et al. |
| 5,727,569 A | 3/1998 | Benetti et al. |
| 5,735,290 A | 4/1998 | Sterman et al. |
| 5,737,500 A | 4/1998 | Seraji et al. |
| 5,737,506 A | 4/1998 | McKenna et al. |
| 5,737,711 A | 4/1998 | Abe |
| 5,738,649 A | 4/1998 | MacOviak |
| 5,740,699 A | 4/1998 | Ballantyne et al. |
| 5,740,802 A | 4/1998 | Nafis et al. |
| 5,743,884 A | 4/1998 | Hasson et al. |
| 5,744,363 A | 4/1998 | Mukherjee et al. |
| 5,748,767 A | 5/1998 | Raab |
| 5,749,362 A | 5/1998 | Funda et al. |
| 5,749,892 A | 5/1998 | Vierra et al. |
| 5,754,741 A | 5/1998 | Wang et al. |
| 5,762,458 A | 6/1998 | Wang et al. |
| 5,765,565 A | 6/1998 | Adair |
| 5,766,126 A | 6/1998 | Anderson |
| 5,769,640 A | 6/1998 | Jacobus |
| 5,776,126 A | 7/1998 | Wilk et al. |
| 5,778,889 A | 7/1998 | Jascomb |
| 5,779,623 A | 7/1998 | Bonnell |
| 5,784,542 A | 7/1998 | Ohm et al. |
| 5,791,908 A | 8/1998 | Gillio |
| 5,792,045 A | 8/1998 | Adair |
| 5,792,135 A | 8/1998 | Madhani et al. |
| 5,792,178 A | 8/1998 | Welch et al. |
| 5,797,900 A | 8/1998 | Madhani et al. |
| 5,800,179 A | 9/1998 | Bailey |
| 5,800,423 A | 9/1998 | Jensen |
| 5,807,243 A | 9/1998 | Vierra et al. |
| 5,807,284 A | 9/1998 | Foxlin |
| 5,807,377 A | 9/1998 | Madhani et al. |
| 5,807,378 A | 9/1998 | Jensen et al. |
| 5,807,379 A | 9/1998 | Lesperance, Jr. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,815,640 A | 9/1998 | Wang et al. |
| 5,817,084 A | 10/1998 | Jensen |
| 5,825,862 A | 10/1998 | Voit et al. |
| 5,825,908 A | 10/1998 | Pieper et al. |
| 5,825,982 A | 10/1998 | Wright et al. |
| 5,827,319 A | 10/1998 | Carlson et al. |
| 5,828,197 A | 10/1998 | Martin et al. |
| 5,828,813 A | 10/1998 | Ohm |
| 5,836,869 A | 11/1998 | Kudo et al. |
| 5,844,824 A | 12/1998 | Newman et al. |
| 5,855,553 A * | 1/1999 | Tajima .................. A61B 34/70 600/407 |
| 5,855,583 A | 1/1999 | Wang et al. |
| 5,859,934 A | 1/1999 | Green |
| 5,860,420 A | 1/1999 | Wiedner et al. |
| 5,860,985 A | 1/1999 | Anschutz |
| 5,860,995 A | 1/1999 | Berkelaar |
| 5,865,730 A | 2/1999 | Fox et al. |
| 5,867,210 A | 2/1999 | Rod |
| 5,876,325 A | 3/1999 | Mizuno et al. |
| 5,878,193 A | 3/1999 | Wang et al. |
| 5,882,206 A | 3/1999 | Gillio |
| 5,885,583 A | 3/1999 | Miyazaki et al. |
| 5,887,121 A | 3/1999 | Funda et al. |
| 5,894,843 A | 4/1999 | Benetti et al. |
| 5,898,599 A | 4/1999 | Massie et al. |
| 5,904,702 A | 5/1999 | Ek et al. |
| 5,906,630 A | 5/1999 | Anderhub et al. |
| 5,907,664 A | 5/1999 | Wang et al. |
| 5,911,036 A | 6/1999 | Wright et al. |
| 5,920,395 A | 7/1999 | Schulz |
| 5,923,770 A | 7/1999 | ODonnell et al. |
| 5,931,832 A | 8/1999 | Jensen |
| 5,938,678 A | 8/1999 | Zirps et al. |
| 5,943,914 A | 8/1999 | Morimoto et al. |
| 5,950,629 A | 9/1999 | Taylor et al. |
| 5,951,475 A | 9/1999 | Gueziec et al. |
| 5,951,587 A | 9/1999 | Qureshi et al. |
| 5,954,692 A | 9/1999 | Smith et al. |
| 5,954,731 A | 9/1999 | Yoon |
| 5,957,831 A | 9/1999 | Adair |
| 5,957,902 A | 9/1999 | Teves |
| 5,971,976 A | 10/1999 | Wang et al. |
| 5,976,122 A | 11/1999 | Madhani et al. |
| 5,980,782 A | 11/1999 | Hershkowitz et al. |
| 5,984,932 A | 11/1999 | Yoon |
| 6,001,108 A | 12/1999 | Wang et al. |
| 6,001,111 A | 12/1999 | Sepetka et al. |
| 6,013,027 A | 1/2000 | Khan |
| 6,017,304 A | 1/2000 | Vierra et al. |
| 6,019,722 A | 2/2000 | Spence et al. |
| 6,024,695 A | 2/2000 | Taylor et al. |
| 6,033,362 A | 3/2000 | Cohn |
| 6,036,641 A | 3/2000 | Taylor et al. |
| 6,038,641 A | 3/2000 | Zangenehpour |
| 6,050,266 A | 4/2000 | Benetti et al. |
| 6,063,021 A | 5/2000 | Hossain et al. |
| 6,080,181 A | 6/2000 | Jensen et al. |
| 6,102,850 A | 8/2000 | Wang et al. |
| 6,102,854 A | 8/2000 | Cartier et al. |
| 6,106,511 A | 8/2000 | Jensen |
| 6,113,534 A | 9/2000 | Koros et al. |
| 6,120,433 A | 9/2000 | Mizuno et al. |
| 6,132,368 A | 10/2000 | Cooper |
| 6,132,441 A | 10/2000 | Grace |
| 6,149,583 A | 11/2000 | Vierra et al. |
| 6,196,081 B1 | 3/2001 | Yau |
| 6,197,017 B1 | 3/2001 | Brock et al. |
| 6,201,984 B1 | 3/2001 | Funda et al. |
| 6,205,716 B1 | 3/2001 | Peltz |
| 6,206,903 B1 | 3/2001 | Ramans |
| 6,210,323 B1 | 4/2001 | Gilhuly et al. |
| 6,213,124 B1 | 4/2001 | Butterworth |
| 6,223,100 B1 | 4/2001 | Green |
| 6,226,566 B1 | 5/2001 | Funda et al. |
| 6,231,526 B1 | 5/2001 | Taylor et al. |
| 6,231,585 B1 | 5/2001 | Takahashi et al. |
| 6,244,809 B1 | 6/2001 | Wang et al. |
| 6,246,200 B1 | 6/2001 | Blumenkranz et al. |
| 6,246,898 B1 | 6/2001 | Vesely et al. |
| 6,254,532 B1 | 7/2001 | Paolitto et al. |
| 6,259,806 B1 | 7/2001 | Green |
| 6,270,453 B1 | 8/2001 | Sakai |
| 6,292,712 B1 | 9/2001 | Bullen |
| 6,307,285 B1 | 10/2001 | Delson et al. |
| 6,309,397 B1 | 10/2001 | Julian et al. |
| 6,312,435 B1 | 11/2001 | Wallace et al. |
| 6,330,837 B1 | 12/2001 | Charles et al. |
| 6,331,181 B1 | 12/2001 | Tierney et al. |
| 6,346,072 B1 | 2/2002 | Cooper |
| 6,346,077 B1 | 2/2002 | Taylor et al. |
| 6,364,888 B1 | 4/2002 | Niemeyer et al. |
| 6,368,332 B1 | 4/2002 | Salcudean et al. |
| 6,371,952 B1 | 4/2002 | Madhani et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,436,107 B1 | 8/2002 | Wang et al. |
| 6,459,926 B1 | 10/2002 | Nowlin et al. |
| 6,464,691 B1 | 10/2002 | Castaneda et al. |
| 6,468,265 B1 | 10/2002 | Evans et al. |
| 6,470,236 B2 | 10/2002 | Ohtsuki |
| 6,490,490 B1 | 12/2002 | Uchikubo et al. |
| 6,496,099 B2 | 12/2002 | Wang et al. |
| 6,522,906 B1 | 2/2003 | Salisbury, Jr. et al. |
| 6,549,926 B1 | 4/2003 | Kalambur et al. |
| 6,574,355 B2 | 6/2003 | Green |
| 6,574,503 B2 | 6/2003 | Ferek-Petric |
| 6,589,164 B1 | 7/2003 | Flaherty |
| 6,646,541 B1 | 11/2003 | Wang et al. |
| 6,659,939 B2 | 12/2003 | Moll et al. |
| 6,699,177 B1 | 3/2004 | Wang et al. |
| 6,699,235 B2 | 3/2004 | Wallace et al. |

(56) References Cited

U.S. PATENT DOCUMENTS

| | | |
|---|---|---|
| 6,714,839 B2 | 3/2004 | Salisbury et al. |
| 6,720,988 B1 | 4/2004 | Gere et al. |
| 6,728,599 B2 | 4/2004 | Wang et al. |
| 6,740,028 B2 | 5/2004 | Boone et al. |
| 6,764,445 B2 | 7/2004 | Ramans et al. |
| 6,793,669 B2 | 9/2004 | Nakamura et al. |
| 6,799,065 B1 | 9/2004 | Niemeyer |
| 6,817,972 B2 | 11/2004 | Snow |
| 6,837,883 B2 | 1/2005 | Moll et al. |
| 6,852,107 B2* | 2/2005 | Wang ............... G05B 15/02 600/102 |
| 6,858,003 B2 | 2/2005 | Evans et al. |
| 6,892,112 B2 | 5/2005 | Wang et al. |
| 6,905,460 B2 | 6/2005 | Wang et al. |
| 6,936,001 B1 | 8/2005 | Snow |
| 6,951,535 B2 | 10/2005 | Ghodoussi et al. |
| 7,083,571 B2 | 8/2006 | Wang et al. |
| 7,087,049 B2 | 8/2006 | Nowlin et al. |
| 7,245,202 B2 | 7/2007 | Levin |
| 7,250,028 B2 | 7/2007 | Julian et al. |
| 7,259,652 B2 | 8/2007 | Wang et al. |
| 7,413,565 B2 | 8/2008 | Wang et al. |
| 7,682,357 B2 | 3/2010 | Ghodoussi et al. |
| 7,695,481 B2 | 4/2010 | Wang et al. |
| 7,806,891 B2 | 10/2010 | Nowlin et al. |
| 7,865,266 B2 | 1/2011 | Moll et al. |
| 7,914,521 B2 | 3/2011 | Wang et al. |
| RE43,049 E | 12/2011 | Grace |
| 8,105,235 B2 | 1/2012 | Ramans et al. |
| 8,241,306 B2 | 8/2012 | Grace |
| 8,292,916 B2 | 10/2012 | Grace |
| 8,489,235 B2 | 7/2013 | Moll et al. |
| 8,504,201 B2 | 8/2013 | Moll et al. |
| 8,527,094 B2 | 9/2013 | Kumar et al. |
| 8,600,551 B2 | 12/2013 | Itkowitz et al. |
| 8,666,544 B2 | 3/2014 | Moll et al. |
| 8,831,782 B2 | 9/2014 | Itkowitz |
| 8,870,900 B2 | 10/2014 | Julian et al. |
| 8,914,150 B2 | 12/2014 | Moll et al. |
| 9,039,681 B2 | 5/2015 | Wang et al. |
| 9,107,633 B2 | 8/2015 | Mueller et al. |
| 9,119,654 B2* | 9/2015 | Ramans ............ A61B 19/2203 |
| 9,271,798 B2 | 3/2016 | Kumar et al. |
| 9,333,042 B2* | 5/2016 | Diolaiti ............. A61B 1/00087 |
| 9,666,101 B2* | 5/2017 | Kumar ................. G09B 23/28 |
| 2002/0029095 A1* | 3/2002 | Kosaka ................ B25J 9/1674 700/245 |
| 2002/0062435 A1 | 5/2002 | Nemirovsky et al. |
| 2002/0140665 A1 | 10/2002 | Gordon |
| 2003/0013949 A1* | 1/2003 | Moll ................ A61B 19/2203 600/407 |
| 2003/0060927 A1* | 3/2003 | Gerbi ................ G06F 19/3406 700/245 |
| 2003/0083648 A1 | 5/2003 | Wang et al. |
| 2005/0107808 A1 | 5/2005 | Evans et al. |
| 2005/0228365 A1 | 10/2005 | Wang et al. |
| 2006/0166681 A1 | 7/2006 | Lohbihler |
| 2006/0178559 A1* | 8/2006 | Kumar ................. G09B 23/28 600/109 |
| 2008/0046122 A1 | 2/2008 | Manzo et al. |
| 2008/0228196 A1 | 9/2008 | Wang et al. |
| 2008/0312668 A1 | 12/2008 | Grace |
| 2009/0036902 A1* | 2/2009 | DiMaio ............ A61B 19/2203 606/130 |
| 2010/0225209 A1 | 9/2010 | Goldberg et al. |
| 2010/0228249 A1 | 9/2010 | Mohr et al. |
| 2011/0112571 A1 | 5/2011 | Grace |
| 2012/0283745 A1* | 11/2012 | Goldberg ............ A61B 34/30 606/130 |
| 2013/0023899 A1 | 1/2013 | Green |
| 2015/0248847 A1 | 9/2015 | Wang et al. |
| 2016/0166345 A1 | 6/2016 | Kumar et al. |

FOREIGN PATENT DOCUMENTS

| | | |
|---|---|---|
| EP | 0239409 A1 | 9/1987 |
| EP | 0424687 A1 | 5/1991 |
| EP | 0494343 A2 | 7/1992 |
| EP | 0494943 B1 | 8/1995 |
| EP | 0732082 A2 | 9/1996 |
| EP | 0776738 B1 | 4/2002 |
| EP | 2016908 A2 | 1/2009 |
| EP | 1131004 B1 | 10/2009 |
| EP | 2138105 A2 | 12/2009 |
| EP | 2298222 A2 | 3/2011 |
| JP | H11262492 A | 9/1999 |
| WO | WO-9104711 A1 | 4/1991 |
| WO | WO-9220295 A1 | 11/1992 |
| WO | WO-9313916 A1 | 7/1993 |
| WO | WO-9418881 A1 | 9/1994 |
| WO | WO-9426167 A1 | 11/1994 |
| WO | WO-9501757 A1 | 1/1995 |
| WO | WO-9715240 A1 | 5/1997 |
| WO | WO-9729690 A1 | 8/1997 |
| WO | WO-9803954 A1 | 1/1998 |
| WO | WO-9817182 A1 | 4/1998 |
| WO | WO-9825666 A1 | 6/1998 |
| WO | WO-9848704 A1 | 11/1998 |
| WO | WO-199909892 | 3/1999 |
| WO | WO-9916367 A1 | 4/1999 |
| WO | WO-9950721 A1 | 10/1999 |
| WO | WO-200007503 A1 | 2/2000 |
| WO | WO-0015119 A2 | 3/2000 |
| WO | WO-0030548 A1 | 6/2000 |
| WO | WO-0030551 A1 | 6/2000 |
| WO | WO-0033726 A1 | 6/2000 |
| WO | WO-0015119 A9 | 8/2000 |
| WO | WO-0030548 B1 | 9/2000 |
| WO | WO-0059384 A1 | 10/2000 |
| WO | WO-0030551 A9 | 11/2000 |
| WO | WO-0015119 A3 | 5/2001 |
| WO | WO-0030548 A8 | 7/2001 |
| WO | WO-0030548 A9 | 8/2002 |

OTHER PUBLICATIONS

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992, 1 page.

Abstract of a presentation given at the 3rd World Congress of Endoscopic Surgery in Bordeaux entitled "Session 15/1", Jun. 18-20, 1992, 1 page.

Abstract of a presentation given at the 3rd World Congress of Endoscopic Surgery in Bordeaux, entitled "Session 15/2", Jun. 18-20, 1992, 1 page total.

Abstract of a presentation given at the 3rd World Congress of Endoscopic Surgery in Bordeaux entitled "Session 15/4", Jun. 18-20, 1992, 1 page.

Abstract of a presentation given at the 3rd World Congress of Endoscopic Surgery in Bordeaux entitled "Session 15/5", Jun. 18-20, 1992, 1 page.

Adachi, Yoshitaka, "Touch and Trace on the Free-Form Surface of Virtual Objects, Research & Development Center," Suzuki Motor Corporation, Yokohama, Japan, Sep. 18-22, 1993, pp. 162-168, IEEE.

Alexander, Arthur D., "A Survey Study of Teleoperators Robotics and Remote Systems Technology," Remotely Manned Systems Exploration and Operation in Space, California Institute of Technology, 1973, pp. 449-458.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Anderson, Robert J., "Bilateral Control of Teleoperators with Time Delay," IEEE Transactions on Automatic Control, IEEE, 1989, vol. 34, No. 5, pp. 494-501.

(56) References Cited

OTHER PUBLICATIONS

Asada Haruhiko et al., "Development of a direct drive arm using high torque brushless motors," Proc. of 1st Int. Symp. on Robotics Research, 1984, pp. 583-599, Chapter 7, MIT Press.

Askew, Scott R. et al., "Ground control testbed for space station freedom robot manipulators," IEEE Virtual Reality Annual International Symposium, 1993, pp. 69-75, IEEE.

B-1 Bomber Simulator, 8 pages [online], [retrieved on Jun. 28, 2013]. Retrieved from the Internet:< URL: http://www.seeingtheusa.com/2012/10/b-1-bomber-simulator.html>.

Baumann, Roger, "Haptic Interface for Virtual Reality Based Laparoscopic Surgery Training Environment," Theses No. 1734 Ecole Pholytechnique Federale de Lausanne, 1997, 104 Total Pages.

Bejczy, Antal K. et al., "A synchronized computational architecture for generalized bilateral control of robot arms," SPIE Space Station Automation III, 1987, pp. 123-134, vol. 851.

Bejczy, Antal K. et al., "Controlling Remote Manipulators through Kinesthetic Coupling," Computers in Mechanical Engineering, 1983, pp. 48-60, vol. 1-Issue 1.

Ben Gayed, M. et al., "An Advanced Control Micromanipulator for Surgical Application," Systems Science, 1987, pp. 23-34, vol. 13 No. 1-2ol 13 No. 1-2.

Ben Gayed, M. et al., "An Advanced Control Micromanipulator for Surgical Applications," Systems Science, 1987, pp. 123-134, vol. 13.

Besant, Colin et al., Abstract of presentation "Camera Control for Laparoscopic Surgery by Speech recognizing Robot: Constant Attention and Better Use of Personnel," 3rd World Congress of Endoscopic surgery, 1992, p. 271, vol. 3—issue 3.

Bose, Bijo et al., "Tremor compensation for robotics assisted microsurgery," Annual Intl Conf. of IEEE Engineering in Medicine and Biology Society, Oct.-Nov. 1992, pp. 1067-1068, vol. 14—Issue 3, IEEE.

Bowersox, Jon C. et al., "Vascular applications of telepresence surgery: Initial feasibility studies in swine," J. Vascular Surgery, Feb. 1996, pp. 281-287, vol. 23—Issue 2.

Butner, Steven E. et al., "A real-time system for tele-surgery," IEEE 21st International Conference on Distributed Computing Systems, 2001, pp. 236-243, IEEE.

Cavusoglu, Murat Cenk et al., "A Laparoscopic Telesurgical Workstation," IEEE Transactions on Robotics and Automation, Aug. 1999, vol. 15, Issue 4, pp. 728-739.

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

Christensen, B. et al., "Model based sensor directed remediation of underground storage tanks," International Conf. on Robotics and Automation, Sacramento, CA, Apr. 1991, pp. 1377-1383, vol. 2. IEEE.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Colgate, J. Edward, "Robust Impedance Shaping Telemanipulation," IEEE Transactions on Robotics and Automation, 1993, pp. 374-384, vol. 9—No. 4, IEEE.

Computer Motion, Inc., "AESOP: Automated Endoscopic System for Optimal Positioning," Press Release, 1994, 2 pages.

Computer Motion, Inc., "Automated Endoscopic System for Optimal Positioning," Enhancing Performance Through Robotics, Date Unknown, 2 pages.

Co-pending U.S. Appl. No. 60/111,710, filed Dec. 8, 1998.
Co-pending U.S. Appl. No. 60/111,711, filed Dec. 8, 1998.
Co-pending U.S. Appl. No. 60/111,713, filed Dec. 8, 1998.
Co-pending U.S. Appl. No. 60/111,714, filed Dec. 8, 1998.
Co-pending U.S. Appl. No. 60/116,891, filed Jan. 22, 1999.

Corcoran, Elizabeth, "Robots for the Operating Room," The New York Times, 2 pages total, Jul. 19, 1992, Section 3 p. 9C.

Das, Hari et al., "Kinematic Control and Visual Display of Redundant Teleoperators," IEEE International Conference on Systems, Man, and Cybernetics, 1989, pp. 1072-1077, vol. 3, IEEE.

Dolan, J.M. et al., "A Robot in an Operating Room: A Bull in a China Shop," 1987, pp. 1096-1097, vol. 2.

Elder, Matthew C. et al., "Specifying user interfaces for safety critical medical systems," Second Annual International Symposium on Medical Robotics and Computer Assisted Surgery, Nov. 1995, pp. 148-155.

Finlay, Patrick A., "Orthosista, An Active Surgical Localiser for Assisting Orthopaedic Fracture Fixation," Proceedings of the Second Annual International Symposium on Medical Robotics and Computer Assisted Surgery; Baltimore, MD; Nov. 4-7, 1995, pp. 203-207.

Fu, K.S. et al., "Robotics: control, sensing, vision, and intelligence," 1987, pp. 12-76 and 201-265, Ch. 2 & 5, McGraw-Hill Book Company.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Galloway, Robert L. et al., "A new device for interactive image guided surgery," Proceedings the International Society of Optical Engineering SPIE Medical Imaging V: Image Capture Formatting and Display Kim Y Ed, 1991, pp. 9-18, vol. 1444, SPIE.

Goertz, Ray et al., "ANL mark E4A electric master slave manipulator," Proc 14th Conf. on Remote System Technology, 1966, pp. 115-123.

Graves, Sean et al., "Dynamic Session Management for Telerobotic Control and Simulation," IEEE International Conference on Robotics and Automation, 1994, pp. 1740-1745, vol. 2, IEEE.

Green, Philip S., "A Pneumatic Controlled Sewing Device for Endoscopic Application the MIS Sewing Instrument MSI," Abstract No. 7, 1992.

Green, Philip S. et al., Abstract of a presentation, "Telepresence: Advanced Teleoperator Technology for Minimally Invasive Surgery," 1992 Medicine Meets Virtual Reality (MMVR) symposium in San Diego, Jun. 4-7, 1992, 1 page.

Green, Philip S. et al., Abstract of a presentation "Telepresence: Advanced Teleoperator Technology for Minimally Invasive Surgery," given at the 3rd World Congress of Endoscopic Surgery in Bordeaux, Jun. 18-20, 1992, 2 pages total, abstract 704.

Green, Philip, S. et al., "Mobile telepresence surgery," 2nd Annual Intl Symposium on Med. Robotics and Computer Assisted Surgery, Maryland Nov. 1995, pp. 97-103.

Green, Philip S. et al., Statutory Declaration by Dr. Phillip S. Green, the presenter of the video entitled "Telepresence Surgery: The Future of Minimally Invasive Medicine," European Patent Convention in the Matter of EP-B-653922. 32 pages, Sep. 12, 2000.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Guo, Shuxinng et al., "Micro active guide wire catheter system—characteristic evaluation, electrical model and operability evaluation of micro active catheter," Sixth International IEEE Symposium on Micro Machine and Human Science, 1995, pp. 131-136, IEEE.

Guthart, Gary S. et al., "The IntuitiveT telesurgery system: overview and application," Proceedings of the 2000 IEEE International Conference on Robotics & Automation, 2000, pp. 618-621, vol. 1, IEEE.

Hamilton, E.C. et al., "Comparision of Video Trainer and Virtual Reality Training Systems on acquisition of Laparoscopic Skills," Surgical endoscopy, 2001, pp. 406-411, vol. 16, Springer Verlang New York Inc.

Heer, Ewald, "Remotely Manned Systems: Exploration and Operation in Space," Proceedings of the First National Conference Pasadena, CA, Sep. 13-15, 1972, pp. 449-458 and 483-492.

Hill, John, W. et al., "Tactile Perception Studies Related to Teleoperator Systems," Final Report, Contract NAS 2-5409, SRI Project 7948, Stanford Research Institute, Menlo Park, California, 1971, 45 pages.

(56) References Cited

OTHER PUBLICATIONS

Hill, John W. et al., "Telepresence Technology in Medicine: Principles and Applications," Proceedings of IEEE, 1998, vol. 86—Issue 3, pp. 569-580, IEEE.
Hill, John W., "Telepresence surgery demonstration system," Robotics and Automation, 1994, pp. 2302-2307, vol. 3, SRI International.
Hogan, Neville, "Controlling Impedance at the Man/Machine Interface," IEEE International Conference on Robotics and Automation, 1989, pp. 1626-1631, vol. 3, IEEE.
Holler, Elmar et al., "An ATM based local communication system for telesurgery," Interactive Tech. and New Paradigm Healthcare, 1995, pp. 137-146.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian, W. et al., "Manipulation and dynamic mechanical testing of microscopic objects using a tele-micro-robot system," IEEE Control Systems Magazine, 1990, pp. 3-9, vol. 10—Issue 2, IEEE.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Ikuta, Koji et al., "Hyper redundant active endoscope for minimum invasive surgery," pp. 230-237, Proc. IEEE the First International Conference on Medical Robot and Computer Aided Surgery (MRCAS'94), (1994).
Imaida, Takashi et al., "Ground-Space Bilateral Teleoperation of ETS-VII Robot Arm by Direct Bilateral Coupling Under 7-s Time Delay Condition," IEEE Transactions on Robotics and Automation, 2004, pp. 499-511, vol. 20—No. 3,IEEE.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
Iwata, Hiroo, "Pen based haptic virtual environment," IEEE Institute of Engineering Mechanics U. of Tsukuba Japan, 1993, pp. 287-292, IEEE.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jau, B. M., "Anthropomorphic Remote Manipulator," NASA Tech Briefs, Apr. 1991, p. 92, NASA's Jet Propulsion Laboratory, Pasadena, California.
Kazerooni, H. , "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator," Robotics and Computer-Integrated Manufacturing, 1989, pp. 287-293, vol. 6, Issue 4.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kazerooni, H, "Human/Robot Interaction via the Transfer of Power and Information Signals—Part II," An Experimental Analysis, Proc. of the 1989 IEEE International Conference on Robotics and Automation, 1989, pp. 1641-1647, vol. 3, IEEE.
Kim, Won S., "Developments of New Force Reflecting Control Schemes and an Application to a Teleoperation Training Simulator," Proceedings of the 1992 IEEE International Conference on Robotics and Automation, 1992, pp. 1412-1419, vol. 2, IEEE.
Kirklin, John W. et al., "Cardiac Surgery," 1993, 4 Pages Total, vol. 1 and 2, Second ed John Wiley and Sons Inc N Y (Table of Contents).
Kosuge, Kazuhiro, "Bilateral Feedback Control of Telemanipulators via Computer Network," IEEE International Conference on Intelligent Robots and Systems, 1996, pp. 1380-1385. vol. 3, IEEE.
Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20, 1992, 1 page.
Landreneau, Rodney J. et al., "Video Assisted Thoracic Surgery: Basic Technical Concepts and Intercostal Approach Strategies," The Annals of Thoracic Surgery, 1992, pp. 800-807, vol. 54—Issue 4, The Society of Thoracic Surgeons.
Lappalainen J., et al., Direct Connection of Simulator and DCS Enhances Testing and Operator Training, 8 pages, [online], [retrieved on Jul. 2, 2013]. Retrieved from the Internet: < URL: http://www.tappi.org/Downloads/unsorted/UNTITLED-ENG99495pdf.aspx>.
Lavallee, Stephane, "A New System for Computer Assisted Neurosurgery," IEEE Eng. in Med. & Biol. Soc. 11th Annual International Conference, Jun. 1989, pp. 926-927, vol. 11.
Lazarevic, Zoran, "Feasibility of a Stewart Platform with Fixed Actuators as a Platform for CABG Surgery Device," 1997, 45 pages, Master's Thesis Columbia University Department of Bioengineering.
Liu, Alan et al., "A Survey of Surgical Simulation: Applications, Technology and Education," Presence, 2003, pp. 599-614, MIT Press.
Mack, Michael J. et al., "Video-assisted coronary bypass grafting on the beating heart," The Annals of thoracic surgery, 1997, pp. S100-S103, vol. 63 (6 Suppl).
Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.
Madhani, Akhil, "Thesis Proposal: Force-Reflecting Teleoperated Endoscopic Surgery," 1995, pp. 1-6 w/attachments pp. 1-2.
Mair, Gordon M., Industrial Robotics, Prentice Hall, 1988, pp. 41-43, 49-50, 54, 203-209.
Majima S. et al., "On a Micro Manipulator for Medical Application Stability Consideration of its Bilateral Controller Mechatronics," 1991, pp. 293-309, vol. 1—Issue 3.
Medical Simulation, 7 pages, [online], [retrieved on Jul. 2, 2013]. Retrieved from the Internet< URL: http://en.wikipedia.org/wiki/Medical_simulation>.
Melzer, Abstract of a presentation "Concept and Experimental Application of a Surgical Robotic System the Steerable MIS Instrument SMI," given at the 3rd World Congress of Endoscopic Surgery in Bordeaux, Jun. 18-20, 1992, 1 page total.
Michael B. Cohn's Home Page, http://ww-bsac.ees.berkeley.edu/users/michaelc/, downloaded Nov. 1, 1996, p. 1; UC Berkeley/Endorobotics Corporation Surgical Robotics Project Job Openings, http:/www-bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.
Moravec, Hans, Peter, "Obstacle Avoidance and Navigation in the Real World by a Seeing Robot Rover," PhD thesis, 1980, Chapter 3, pp. 13-18, Stanford University.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Nudehi, Shahin S. et al., "A Shared-Control Approach to Haptic Interface Design for Minimally Invasive Telesurgical Training," IEEE Transactions on Control Systems Technology, 2005, pp. 588-592, vol. 13—No. 4, IEEE.
Preising, B. et al., "A Literature Review: Robots in Medicine," IEEE Engineering in Medicine and Biology, 1991, pp. 13-22, 71, vol. 10—Issue 2, IEEE.
Rasor, Ned S. et al., "Endocorporeal Surgery Using Remote Manipulators," Proceedings of the First National Conference held at California Institute of Technology, 1972, pp. 483-492.
Richardson, I. E. G. et al., "SAVIOUR: Telemedicine in Action," IEE Colloquium on Teleworking and Teleconferencing, 1994, pp. 4/1-4/2, IEEE.
Rosheim, Mark E., Chapter 5: "Pitch-Yaw-Roll Wrists," Robot Wrist Actuators, Wiley & Sons, New York, 1989, pp. 95-206.

(56) References Cited

OTHER PUBLICATIONS

Rovetta, Alberto et al., "The first experiment in the world of robot telesurgery for laparoscopy carried out by means of satellites networks and optical fibers networks on Jul. 7, 1993," 1993, pp. 51-56, vol. 1, IEEE.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Sackier J.M., et al., "Robotically Assisted Laparoscopic Surgery, From Concept to Development," Surgical Endoscopy, Springer-Verlag, 1994, vol. 8 (8), pp. 63-66.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sato, Yoshinobu et al., "The Safety Assessment of Human-Robot Systems(Architectonic principles of hazard-control systems)," JSME International Journal, 1989, pp. 67-74, vol. 32—Issue 1.
Schenker Paul S. et al., "Development of a New High Dexterity Manipulator for Robot Assisted Microsurgery," Proceedings of SPIE, The Intl.Society for Optical Engineering, 1994, pp. 191-198, vol. 2351.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Seymour, Neal E. et al., "Virtual Reality Training Improves Operating Room Performance," Annals of Surgery, 2002, pp. 458-464, vol. 236—No. 4, Lippincott Williams & Wilkins, Inc.
Shimoga, K.B. et al., "Touch and Force Reflection for Telepresence Surgery," Proceedings of the 16th Annual International Conference of the IEEE Engineering in Medicine and Biology Society, Engineering Advances: New Opportunities for Biomedical Engineers, 1994, pp. 1049-1050, vol. 2, IEEE.
Simulation, 22 pages, [online], [retrieved on Jul. 2, 2013]. Retrieved from the Internet:< URL: http://en.wikipedia.org/wiki/Simulation>.
Smith, Warren E. et al., "Correction of Distortion in Endoscope Images," IEEE Transactions on Medical Imaging, Mar. 92, pp. 117-122, vol. 11—Issue 1, IEEE.
Stevens, Jane E., "Cyber Surgery Computers cameras and robots are creating an improved operating system for doctors," Los Angeles Times, Nov. 30, 1995, p. 2.
Sukthankar, Sujat M. et al., "Towards force feedback in laparoscopic surgical tools," IEEE Human Interface Laboratory Dept. of Biomedical Engineering, Ohio, 1994, pp. 1041-1042, IEEE.
Taubes, Gary et al., "Surgery in Cyberspace," Discover magazine, Dec. 1994, vol. 15, issue 12, pp. 85-92.
Taylor R.H., et al., Table of Contents,"Computer-Integrated Surgery," Technology and Clinical Applications, The MIT Press, Cambridge, MA,1996, 8 pages.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer Integrated Surgery: Technology and Clinical Applications," 1996, pp. vii-xii, MIT Press Cambridge MA.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.
Tejima, Noriyuki et al., "A New Microsurgical Robot System for Corneal Transplantation," Precision Machinery, 1988, pp. 1-9, vol. 2, Gordon and Breach Science Publishers Inc.
Tendick Frank, et al., "Analysis of the Surgeon's Grasp for Telerobotic Surgical Manipulation," IEEE 11th Annual Int Conf on Engineering in Medicine and Biology, Jun. 1989, pp. 914-915, IEEE.
Tendick, Frank et al., "Comparison of laproscopic imaging systems and conditions using a knot tying task," Second Annual International Symposium on Medical Robotics and Computer Assisted Surgery, Nov. 4-7, 1995, 9 pages.
Thring, M.W., Robots and Telechirs: Manipulators with Memory; Remote Manipulators; Machine Limbs for the Handicapped, Ellis Horwood Limited, England,1983, 79 pages, including Table of Contents, Preface, Chap. 5 (pp. 108-131), Chap. 7 (pp. 194-195, 235), Chap. 8 (pp. 236-287), Chap. 9 (p. 279).
Transcript of a video presented by SRI at the 3rd World Congress of Endoscopic Surgery in Bordeaux, France on Jun. 18-20, 1992; in Washington D.C. on Apr. 9, 1992; and in San Diego, CA on Jun. 4-7, 1992; entitled "Telepresence Surgery: The Future of Minimally Invasive Medicine," 3 pages.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trinder J. C. et al., "A Close Range Digital Photogrammetry System," 1990, pp. 440-447, vol. 1395, SPIE.
Tsai, Roger Y., "A Versatile Camera Calibration Technique for High-Accuracy 3D Machine Vision Metrology Using Off-the-Shelf TV Cameras and Lenses," IEEE Journal of Robotics and Automation, 1987, pp. 323-344, vol. RA-3—Issue 4, IEEE.
U.S. Appl. No. 09/399,457, filed Sep. 17, 1999 (now abandoned), Ramans, Andris D.
Vertut, Jean and Phillipe Coiffet, Robot Technology: Teleoperation and Robotics Evolution and Development, English translation, Prentice-Hall, Inc., Inglewood Cliffs, NJ, USA 1986; vol. 3A, 332 pages.
Vibet, C., "Properties of Master-Slave Robots," Motor-con, Motorcon'87, Hannover, Apr. 1987, pp. 309-316.
Wapler, M., "Medical manipulators—A Realistic Concept", Minimally Invasive Therapy, 1995, pp. 261-266, vol. 4, Blackwell Science Ltd.
Wolf, Stanley et al., Student Reference Manual for Electronic Instrumentation Laboratories, 1990, pp. 498 and 499, Prentice Hall New Jersey.
Yan, Joseph, et al., "Design and Control of a Motion Scaling System for Microsurgery Experiments," Proc of First Intl Symp on Medical Robotics and Computer Assisted Surgery, 1994, pp. 211-216.
Yan, Joseph et al., "Teleoperation Controller Design Using H Optimization with Application to Motion Scaling," IEEE Transactions on Control Systems Technology, 1996, pp. 244-258, vol. 4—No. 3, IEEE.
Yokokohji, Yasuyoshi and Tsuneo Yoshikawa, "Bilateral Control of Master-Slave Manipulators for Ideal Kinesthetic Coupling Formulation and Experiment," IEEE Transactions on Robotics and Automation, IEEE, 1994, vol. 10, No. 5, pp. 605-620.

\* cited by examiner

|   | U | V | W | X | Y | Z |
|---|---|---|---|---|---|---|
| A | 0 | 0 | 0 | 1 | 0 | 0 |
| B | 0 | 1 | 0 | 0 | 0 | 0 |
| C | 0 | 0 | 1 | 0 | 0 | 0 |
| D | 1 | 0 | 0 | 0 | 0 | 0 |
| E | 0 | 0 | 0 | 0 | 1 | 0 |
| F | 0 | 0 | 0 | 0 | 0 | 1 | fig.12

|   | U | V | W | X | Y | Z |
|---|---|---|---|---|---|---|
| A | 1 | 0 | 0 | 0 | 0 | 0 |
| B | 0 | 1 | 0 | 0 | 0 | 0 |
| C | 0 | 0 | 0 | 0 | 0 | 0 |
| D | 1 | 0 | 0 | 0 | 0 | 0 |
| E | 0 | 0 | 0 | 0 | 1 | 1 |
| F | 0 | 0 | 0 | 0 | 0 | 0 | fig.13

MULTI-USER MEDICAL ROBOTIC SYSTEM FOR COLLABORATION OR TRAINING IN MINIMALLY INVASIVE SURGICAL PROCEDURES

CROSS-REFERENCE TO RELATED APPLICATIONS

This application is a continuation of U.S. patent application Ser. No. 15/006,555, filed Jan. 26, 2016, which is a divisional of U.S. patent application Ser. No. 13/965,581, filed Aug. 13, 2013, now U.S. Pat. No. 9,271,798, which is a divisional of U.S. patent application Ser. No. 11/319,012, filed Dec. 27, 2005, now U.S. Pat. No. 8,527,094, which claims priority from U.S. Provisional Application No. 60/725,770, filed Oct. 12, 2005, which is incorporated herein by this reference.

This application is also a continuation-in-part of U.S. patent application Ser. No. 11/025,766, filed Dec. 28, 2004, which is a continuation of U.S. patent application Ser. No. 10/214,286, filed Aug. 6, 2002, now U.S. Pat. No. 6,858,003, which is a divisional of U.S. patent application Ser. No. 09/436,982, filed Nov. 9, 1999, now U.S. Pat. No. 6,468,265, which claims priority from U.S. Provisional Patent Application No. 60/109,359, filed Nov. 20, 1998, U.S. Provisional Application No. 60/109,301, filed Nov. 20, 1998, U.S. Provisional Application No. 60/109,303, filed Nov. 20, 1998, and U.S. Provisional Application No. 60/150,145, filed Aug. 20, 1999, and which is a continuation-in-part of U.S. patent application Ser. No. 09/433,120, filed Nov. 3, 1999, now U.S. Pat. No. 6,659,939, which is a continuation-in-part of U.S. patent application Ser. No. 09/399,457, filed Sep. 17, 1999, now abandoned, which is a continuation-in-part of U.S. patent application Ser. No. 09/374,643, filed Aug. 16, 1999, now abandoned, which claims priority from U.S. Provisional Patent Application No. 60/116,891, filed Jan. 22, 1999, U.S. Provisional Patent Application No. 60/116,842, filed Jan. 22, 1999, and U.S. Provisional Patent Application No. 60/109,359, filed Nov. 20, 1998, all of which are incorporated herein by this reference.

This application is also a continuation-in-part application of U.S. patent application Ser. No. 10/948,853, filed Sep. 23, 2004, now U.S. Pat. No. 7,413,565, which is a divisional of U.S. patent application Ser. No. 10/246,236, filed Sep. 17, 2002, now U.S. Pat. No. 6,951,535, which is a continuation of U.S. patent application Ser. No. 10/051,796, filed Jan. 16, 2002, now U.S. Pat. No. 6,852,107, all of which are incorporated herein by this reference.

FIELD OF THE INVENTION

The present invention generally relates to minimally invasive robotic surgery systems and in particular, to a multi-user medical robotic system for collaboration or training in minimally invasive surgical procedures.

BACKGROUND OF THE INVENTION

While clinical growth of laparoscopic procedures has stalled, tele-operated robotic surgical systems have been successful in achieving greater procedure development and clinical acceptance in several surgical fields. Two examples of such surgical robotic systems include the da Vinci® Surgical System of Intuitive Surgical, Inc., Sunnyvale, Calif., and the Aesop® and Zeus® robot systems of Computer Motion, Inc., which has been acquired by Intuitive Surgical, Inc.

For example, the da Vinci® surgical system can be used for a wide variety of surgical procedures such as mitral valve repair, Nissen Fundoplication for the treatment of GERD disease, gastric bypass surgery for obesity, radical prostatectomy (da Vinci® Prostatectomy) for the removal of the prostate, esophageal surgery, thymectomy for myasthenia gravis, and epicardial pacemaker leads for biVentricular resynchronization.

Minimally invasive surgery offers many benefits over traditional open surgery techniques, including less pain, shorter hospital stays, quicker return to normal activities, minimal scarring, reduced recovery time, and less injury to tissue. Consequently, demand for minimally invasive surgery is strong and growing.

Since robotic minimally invasive surgery ("RMIS") is still a nascent field, however, there are no commercially available training systems that allow a trainee and mentor to experience the same environment, and physically interact as they would in open or even conventional laparoscopic surgery training. Instead, current RMIS training consists of training courses explaining the robotic device and surgical technique accompanied by laboratory practice in animal and cadaver models, followed by watching already proficient surgeons perform the procedure. A proficient surgeon then assists/supervises the newly trained surgeon during his or her initial procedures.

In a tele-robotic paradigm, this mentoring problem can be generalized irrespective of the location of the two surgeons. However, when they are collocated, the ability to view the surgical scene together, combined with the ability to exchange or share control of the instruments can enable physical interaction between the trainee and the mentor, and provide a superior training environment.

OBJECTS AND SUMMARY OF THE INVENTION

Thus, a multi-user medical robotic system which allows a mentor surgeon to communicate with trainee surgeons, to see the same surgical site as the trainee surgeons, to share control of robotically controlled surgical instruments with the trainee surgeons so that they may feel through their controls what the mentor surgeon is doing with his/hers, and to switch control to selected ones of the trainee surgeons and over-ride that control if necessary during the performance of a minimally invasive surgical procedure, would be highly beneficial for training purposes.

In addition, such a multi-user medical robotic system would also be useful for collaborative surgery in which multiple surgeons work together as a team (i.e., in collaboration) to perform a minimally invasive surgical procedure.

Accordingly, one object of the present invention is to provide a multi-user medical robotic system that facilitates collaboration between surgeons while performing minimally invasive surgical procedures.

Another object is to provide a multi-user medical robotic system that facilitates training of surgeons to perform minimally invasive surgical procedures.

These and additional objects are accomplished by the various aspects of the present invention, wherein briefly stated, one aspect is a medical robotic system comprising: first master input device configured to generate a first command indicative of manipulation of the first master input device by a first user; second master input device configured to generate a second command indicative of manipulation of the second master input device by a second user; first slave robotic mechanism configured to manipulate a first surgery-related device according to a first slave command; at least one processor configured to generate the first slave command by switchably using one or both of the first command and the second command; and an audio system configured for audio communication between the first user and the second user.

Another aspect is a multi-user medical robotic system for collaboration in minimally invasive surgical procedures, comprising: first and second master input devices; first and second slave robotic mechanisms; a switch mechanism operable by a first operator for selectively associating the first and the second slave robotic mechanisms with the first and the second master input devices so that the first operator manipulating the first master input device and a second operator manipulating the second master input device may perform a minimally invasive surgical procedure at a surgical site in collaboration with each other; and first and second headsets respectively worn by the first and the second operators so that they may communicate with each while performing the minimally invasive surgical procedure in collaboration with each other.

Another aspect is a multi-user medical robotic system for training in minimally invasive surgical procedures, comprising: mentor and trainee master input devices respectively manipulatable by a mentor and a trainee; a first slave robotic mechanism; a switch mechanism operable by the mentor for selectively associating the first slave robotic mechanism with the mentor master input device and the trainee master input device so that either or both the mentor or the trainee may control operation of the first slave robotic mechanism to perform a minimally invasive surgical procedure; and a mentor microphone proximate to the mentor and a trainee hearing device proximate to the trainee so that the mentor may speak to the trainee while the mentor is performing the minimally invasive surgical procedure.

Additional objects, features and advantages of the various aspects of the present invention will become apparent from the following description of its preferred embodiment, which description should be taken in conjunction with the accompanying drawings.

BRIEF DESCRIPTION OF THE DRAWINGS

FIGS. 12 and 13 illustrate routing tables corresponding to the master/slave associations of FIGS. 9 and 8, respectively, of an association module utilizing aspects of the present invention.

DETAILED DESCRIPTION OF THE PREFERRED EMBODIMENT

Figure 1:
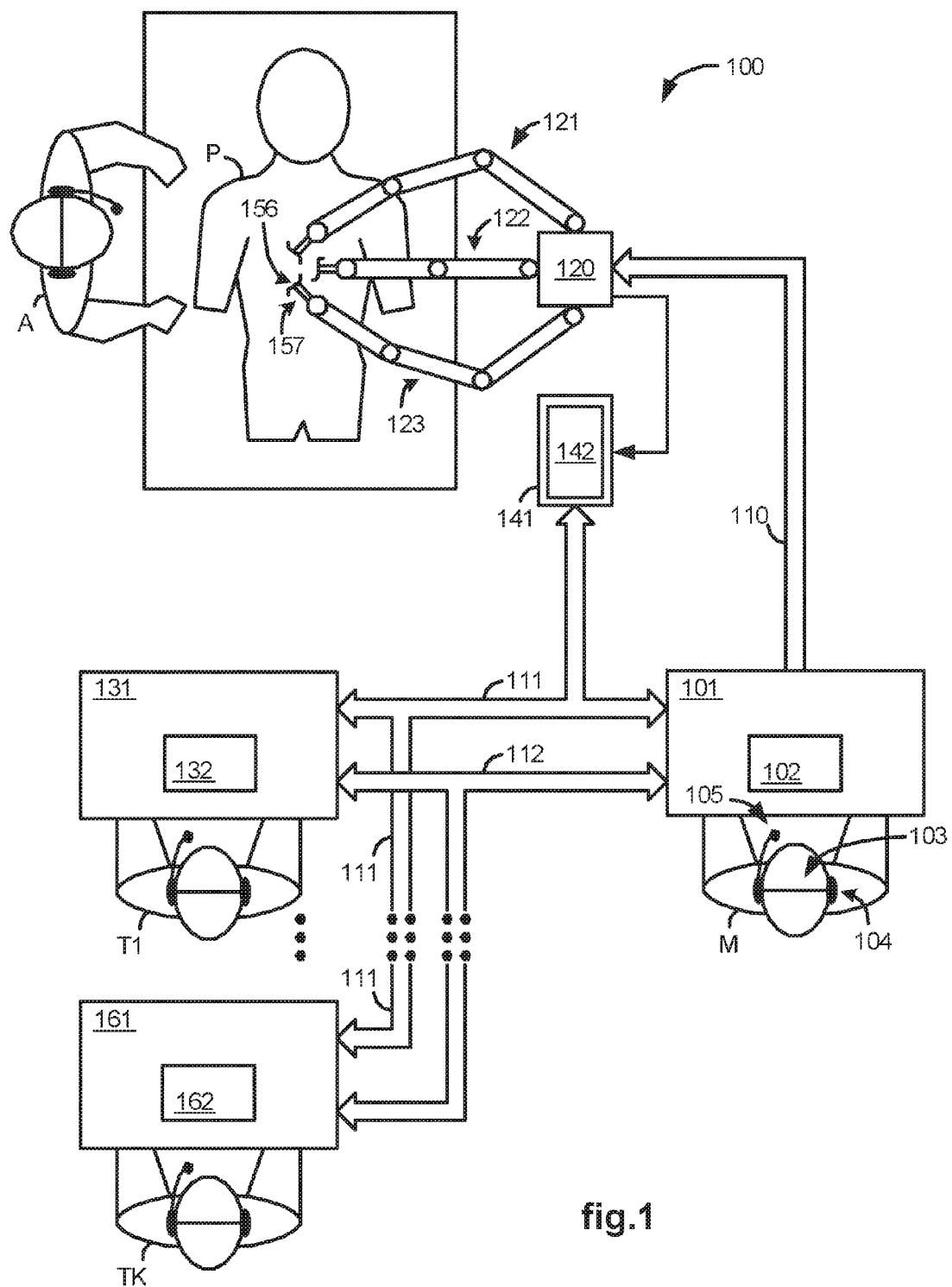
FIG. 1 illustrates a top view of a multi-user medical robotic system for collaboration or training in minimally invasive surgical procedures, utilizing aspects of the present invention.

FIG. 1 illustrates, as an example, a multi-user medical robotic system 100 useful for collaboration or training in minimally invasive surgical procedures. For example, in a collaborative operation, a team of two or more proficient surgeons may work together to perform a minimally invasive surgical procedure, or an expert surgeon may advise a primary surgeon performing a minimally invasive surgical procedure. In a hands-on training environment, a mentor surgeon may act as a mentor or teacher to train one or more trainee surgeons in minimally invasive surgical procedures.

Although configured in this example for a local environment with all participants locally present, the multi-user medical robotic system 100 may also be configured through a network connection for remote participation by one or more participants. For example, a remote surgeon may provide guidance or support to a primary surgeon at a local operating site. In such case, the advising surgeon may share the immersive audio/video environment with the primary surgeon, and may access the surgical instruments as desired by the primary surgeon.

Although a training example is described herein, the described components and features of the system 100 are also useful in collaborative surgery. In particular, it is useful for a lead surgeon in the case of a collaborative procedure to control the selective association of certain surgical tools and/or an endoscope with any one of the participating surgeons during a minimally invasive surgical procedure, just as it is for a mentor surgeon in the case of a training session to control the selective association of certain surgical tools and/or an endoscope with any one of the trainee surgeons during a minimally invasive surgical training session. Also, it is useful in both the collaboration and training environments for all participants to be able to view the surgical site and to communicate with each other during the surgical procedure or training session.

In reference to FIG. 1, a Mentor Surgeon (M) instructs or mentors one or more Trainee Surgeons, such as (T1) and (TK), in minimally invasive surgical procedures performed on a real-life or dummy Patient (P). To assist in the surgical procedures, one or more Assistant Surgeons (A) positioned at the Patient (P) site may also participate.

The system 100 includes a mentor master control station 101 operative by the Mentor Surgeon (M), a slave cart 120 having a plurality of slave robotic mechanisms (also referred to as "robotic arm assemblies" and "slave manipulators") 121~123, and one or more trainee master control stations, such as trainee master control stations 131 and 161, operative by Trainee Surgeons, such as Trainee Surgeons (T1) and (TK). The mentor master control station 101, in this example, communicates directly with the slave cart 120, and the trainee master control stations communicate indirectly with the slave cart 120 through the mentor master control station 101.

The slave cart 120 is positioned alongside the Patient (P) so that surgery-related devices (such as 157) included at distal ends of the slave robotic mechanisms 121~123 may be inserted through incisions (such as incision 156) in the Patient (P), and manipulated by one or more of the participating surgeons at their respective master control stations to perform a minimally invasive surgical procedure on the Patient (P). Each of the slave robotic mechanisms 121~123 preferably includes linkages that are coupled together and manipulated through motor controlled joints in a conventional manner.

Although only one slave cart 120 is shown being used in this example, additional slave carts may be used as needed. Also, although three slave robotic mechanisms 121~123 are shown on the cart 120, more or less slave robotic mechanisms may be used per slave cart as needed.

A stereoscopic endoscope is commonly one of the surgery-related devices included at the distal end of one of the slave robotic mechanisms. Others of the surgery-related devices may be various tools with manipulatable end effectors for performing the minimally invasive surgical procedures, such as clamps, graspers, scissors, staplers, and needle holders.

Use of the stereoscopic endoscope allows the generation and display of real-time, three-dimensional images of the surgical site. Although the stereoscopic endoscope is preferred for this reason, a monoscopic endoscope may alternatively be used where either three-dimensional images are not needed or it is desirable to reduce communication bandwidth requirements.

Alternatively, the system may include multiple endoscopes providing each individual surgeon with a desired view of the workspace. Advantageously, the multiple endoscopes may even be packaged in a single instrument, but with separate steerable camera tips. Optionally, these multiple endoscopes may provide different fields of view such as using a very wide field of view (e.g. with a fish-eye lens) that is appropriately rectified before being displayed to the surgeon.

To facilitate collaboration between surgeons or training of trainee surgeons in minimally invasive surgical procedures, each of the participating surgeons has an associated display to view the surgical site, and a communication means such as a microphone and earphone set to communicate with other participating surgeons.

More particularly, a display 102 is provided with or integrated into the mentor master control station 101, a display 132 is provided with or integrated into the trainee master control station 131, and a display 142 is provided on a vision cart 141 which is in view of the one or more Assistant Surgeons (A), so that the Mentor Surgeon (M), the Trainee Surgeon (T), and the Assistant Surgeon(s) (A) may view the surgical site during minimally invasive surgical procedures.

The vision cart 141, in this example, includes stereo camera electronics which convert pairs of two-dimensional images received from the stereoscopic endoscope into information for corresponding three-dimensional images, displays one of the two-dimensional images on the display 142 of the vision cart 141, and transmits the information of the three-dimensional images over a stereo vision channel 111 to the master control stations of participating surgeons, such as the mentor master control station 101 and the trainee master control stations, for display on their respective displays. For displaying stereo information using properly configured conventional displays, the vision cart 141 may contain devices for frame synchronization, and in that case, conventional video cables may be sufficient for sharing this information between collocated surgeons.

The communication means provided to each of the participants may include individual microphone and earphones (or speaker) components, or alternatively, individual headphone sets, such as headphone set 103 shown as being placed on the head of the Mentor Surgeon (M), as part of a conventional audio system. Preferably a duplex audio communication system (microphone and speaker pair) is built into each surgeon's master control station. Alternatively, headsets may be used, including those using wireless communications to provide maximum comfort and freedom of movement to their users or those that may be connected through wires to their respective master control stations or slave cart, which are in turn, are connected together through mentor/slave lines 110 and mentor/trainee lines 112 for voice communications between the Mentor, Trainee and Assistant Surgeons.

In addition to transmitting voice communications, the mentor/slave and the mentor/trainee lines, 110 and 112, also transmit data. For high bandwidth and low latency communication, the lines 110 and 112, as well as the stereo vision channel lines 111, are preferably composed of fiber optic communication cables/channels, which are especially useful when any of the mentor master control station 101, the trainee master control stations (such as 131 and 161), and the slave cart 120 are remotely situated from the others. On the other hand, for co-located surgeons, normal shielded video and audio cables may be sufficient, while fiber optical communication channels may be used for the mentor/slave or mentor/trainee data transfer lines.

Figure 2:
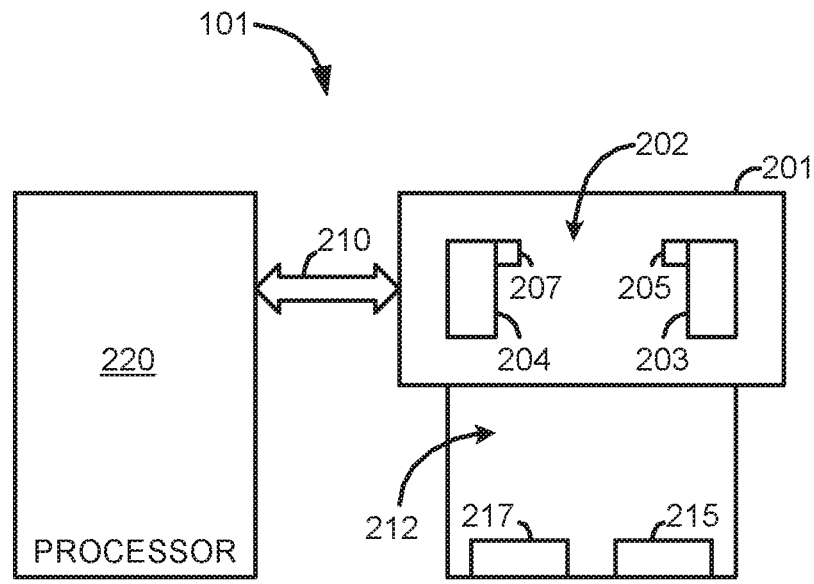
FIGS. 2-3 illustrate simplified front views respectively of mentor and trainee master control stations configured to utilize aspects of the present invention.
Figure 3:
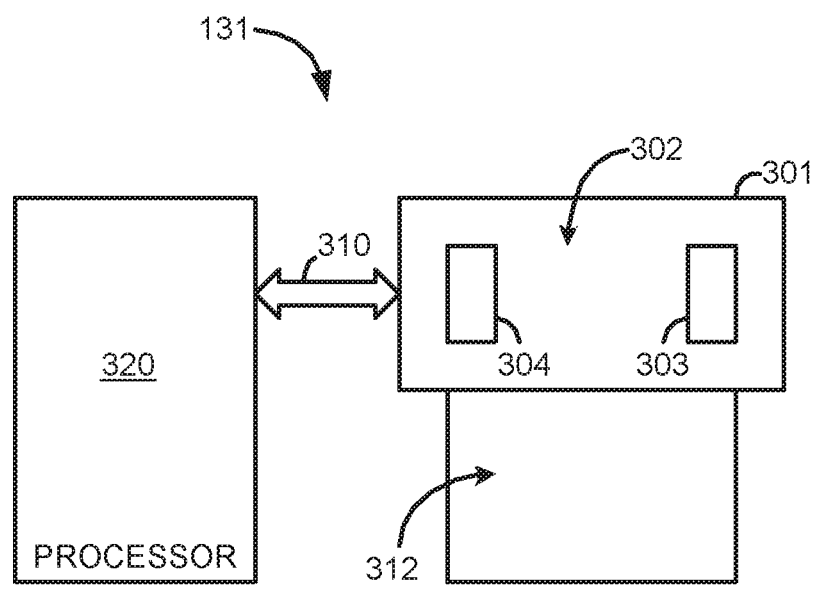

FIGS. 2-3 illustrate simplified front views of the mentor master control station 101 and the trainee master control station 131. The mentor master control station 101 includes right and left master input devices, 203 and 204, whose manipulations by the Mentor Surgeon (M) are sensed by sensors (not shown) and provided to an associated processor 220 via an instrumentation bus 210. Similarly, the trainee master control station 131 includes right and left master input devices, 303 and 304, whose manipulations by the Trainee Surgeon (T1) are sensed by sensors (not shown) and provided to an associated processor 320 via an instrumentation bus 310. Each of the master input devices (also referred to herein as "master manipulators") may include, for example, any one or more of a variety of input devices such as joysticks, gloves, trigger-guns, hand-operated controllers, and the like.

The mentor master control station 101 is preferably configured with one or more switch mechanisms to allow the Mentor Surgeon (M) to selectively associate individual of the slave robotic mechanisms 121-123 with any of the master input devices of the mentor master control station 101 and the trainee master control stations. As one example, two switch mechanisms may be activated by right or left buttons, 205 and 207, positioned on the right and left master input devices, 203 and 204, so as to be manipulatable by right and left thumbs of the Mentor Surgeon (M).

As another example, two switch mechanisms may be activated by right or left footpedals, 215 and 217, which are positioned so as to be manipulatable by right and left feet of the Mentor Surgeon (M). One switch mechanism may also be voice activated by the Mentor Surgeon (M) using his headset 103 or another microphone (not shown), which is coupled to the processor 220 so that it may perform voice recognition and processing of the spoken instructions of the Mentor Surgeon (M).

For complex associations of various aspects of system master input devices and slave robotic mechanisms, a simple binary switch (or combinations of switches) may not be suitable. In such cases, a more flexible association selector may be required, such as a menu of available options displayed on the display 102 of the mentor master control station 101 that the Mentor Surgeon (M) may select from, by using a conventional pointing device, touch screen, or voice activation. The master input devices or input devices built into the master input devices may also be used for this purpose.

To perform a minimally invasive surgical procedure, the operating surgeons perform the procedure by manipulating their respective master input devices which in turn, causes associated slave robotic mechanisms to manipulate their respective surgery-related devices through minimally invasive incisions in the body of the Patient (P) while the surgeons view the surgical site through their respective displays.

The number of surgery-related devices used at one time and consequently, the number of slave robotic mechanisms in the system 100 will generally depend on the diagnostic or surgical procedure and the space constraints within the operating room among other factors. If it is necessary to change one or more of the surgery-related devices being used during a procedure, the Assistant (A) may remove the surgery-related device that is no longer needed from the distal end of its slave robotic mechanism, and replace it with another surgery-related device from a tray of such devices in the operating room. Alternatively, a robotic mechanism may be provided for the surgeon to execute tool exchanges using his/her master input device.

Preferably, the master input devices will be movable in the same degrees of freedom as their associated surgery-related devices to provide their respective surgeons with telepresence, or the perception that the master input devices are integral with their associated surgery-related devices, so that their respective surgeons have a strong sense of directly controlling them. To this end, position, force, and tactile feedback sensors are preferably employed that transmit position, force, and tactile sensations from the devices (or their respective slave robotic mechanisms) back to their associated master input devices so that the operating surgeons may feel such with their hands as they operate the master input devices.

To further enhance the telepresence experience, the three-dimensional images displayed on the displays of the master control stations are oriented so that their respective surgeons feel that they are actually looking directly down onto the operating site. To that end, an image of the surgery-related device that is being manipulated by each surgeon appears to be located substantially where the surgeon's hands are located even though the observation points (i.e., the endoscope or viewing camera) may not be from the point of view of the image.

Figure 4:
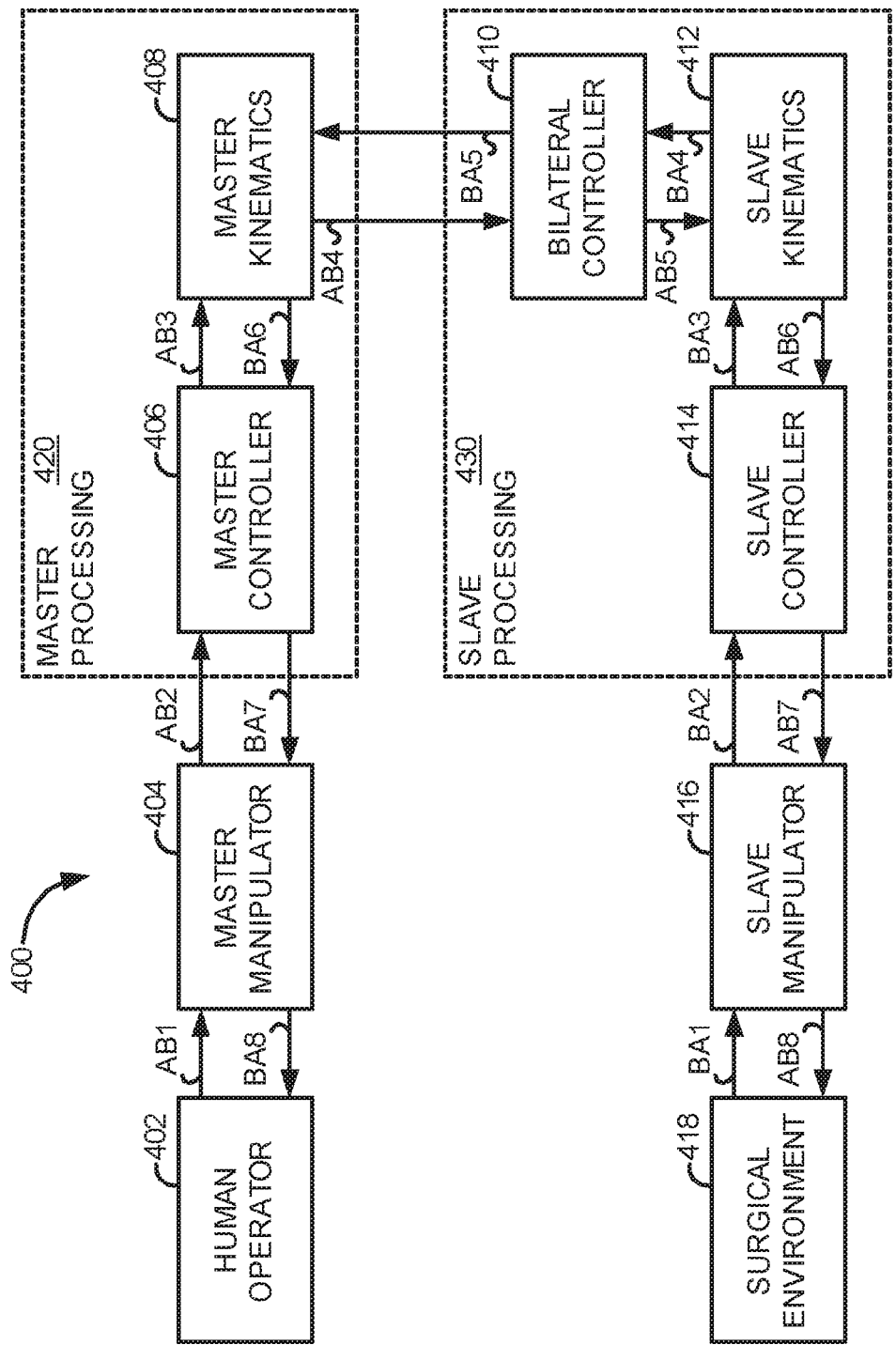
FIG. 4 illustrates a block diagram of a master/slave control system included in the multi-user medical robotic system, utilizing aspects of the present invention.

FIG. 4 illustrates, as an example, a block diagram of a master/slave control system 400 for an associated master manipulator and slave manipulator pair. An example of such a master/slave manipulator pair is the master device input 203 of the mentor master control station 101 and the slave robotic mechanism 121. Master manipulator inputs and corresponding slave manipulator outputs are indicated by arrows AB, and slave manipulator inputs and corresponding master manipulator outputs in the case of feedback are indicated by arrows BA.

Although the master processing unit 420 and slave processing unit 430 described herein may be implemented as analog circuitry, preferably they are implemented digitally using conventional Z-transform techniques for sampled data systems and provided in program code executed by processors of master control stations associated with the master and slave manipulators, 404 and 416, as will be described in further detail in reference to FIG. 10.

In the following description, the master manipulator (i.e., master input device) 404 will be referred to as the master and the slave manipulator (i.e., slave robotic mechanism) 416 will be referred to as the slave, to simplify the description. Also, positions sensed by joint encoders in the master manipulator as well as those in the slave manipulator are referred to as "joint space" positions. Furthermore, references to positions and positioned signals may include orientation, location, and/or their associated signals. Similarly, forces and force signals may generally include both force and torque in their associated signals.

For ease of explanation, the master/slave control system 400 will be described from an initial condition in which the master is at an initial position and the slave is at a corresponding initial position. However, in use, the slave tracks the master position in a continuous manner.

Referring to the control system 400, the master is moved from an initial position to a new position corresponding to a desired position of the end effector (located on the distal end of the slave) as viewed by the surgeon on his display. Master control movements are input by the surgeon 402, as indicated by arrow AB1, by applying a force to the master 404 to cause the master 404 to move from its initial position to the new position.

As the master 404 is thus manipulated by the surgeon, signals from the encoders on the master 404 are input to a master controller 406 as indicated by arrow AB2. At the master controller 406, the signals are converted to a joint space position corresponding to the new position of the master. The joint space position is then input to a master kinematics converter 408 as indicated by arrow AB3. The master kinematics converter 408 then transforms the joint space position into an equivalent Cartesian space position. This is optionally performed by a kinematics algorithm including a Jacobian transformation matrix, inverse Jacobian, or the like. The equivalent Cartesian space position is then input to a bilateral controller 410 as indicated by arrow AB4.

Position comparison and force calculation may, in general, be performed using a forward kinematics algorithm which may include a Jacobian matrix. The forward kinematics algorithm generally makes use of a reference location, which is typically selected as the location of the surgeon's eyes. Appropriate calibration or appropriately placed sensors on the master control station can provide this reference information. Additionally, the forward kinematics algorithm will generally make use of information concerning the lengths and angular offsets of the linkage of the master. More specifically, the Cartesian position represents, for example, the distance of the input handle from, and the orientation of the input handle relative to, the location of the surgeon's eyes. Hence, the equivalent Cartesian space position is input into bilateral controller 410 as indicated by AB4.

In a process similar to the calculations described above, the slave position is also generally observed using joint encoders of the slave 416. In an exemplary embodiment, joint encoder signals read from the slave 416 are provided to a slave controller 414, as indicated by BA2, which converts the signals to a joint space position corresponding to the initial position of the slave 416. The joint space position is then input to a slave kinematics converter 412 as indicated by arrow BA3. The slave kinematics converter 412 then transforms the joint space position into an equivalent Cartesian space position.

In this case, the forward kinematics algorithm used by the slave kinematics converter 412 is preferably provided with the referenced location of a tip of a stereoscopic endoscope capturing images of the surgery site to be viewed on the surgeon display. Additionally, through the use of sensors, design specifications, and/or appropriate calibration, this kinematics algorithm incorporates information regarding the lengths, offsets, angles, etc., describing the linkage structure of the slave cart 120, and set-up joints for the slave 416 (i.e., joints used to initially position the slave that are subsequently locked during the procedure) so that the slave Cartesian position transferred to the bilateral controller 410 is measured and/or defined relative to the tip of the stereoscopic endoscope.

At bilateral controller 410, the new position of the master in Cartesian space relative to the surgeon's eyes is compared with the initial position of the tip of the end effector connected at the distal end of the slave 416 in Cartesian space relative to the tip of the stereoscopic endoscope.

Advantageously, the comparison of these relative relationships occurring in the bilateral controller 410 can account for differences in scale between the master input device space in which the master input device 404 is moved as compared with the surgical workspace in which the end effectors on the distal end of the slave robotic mechanism 416 move. Similarly, the comparison may account for possible fixed offsets, should the initial master and slave positions not correspond.

Since the master has moved to a new position, a comparison by the bilateral controller 410 of its corresponding position in Cartesian space with the Cartesian space position of the slave corresponding to its initial position yields a deviation and a new slave position in Cartesian space. This position is then input to the slave kinematics converter 412 as indicated by arrow AB5, which computes the equivalent joint space position commands.

These commands are then input to the slave controller 414 as indicated by arrow AB6. Necessary joint torques are computed by the slave controller 414 to move the slave to its new position. These computations are typically performed using a proportional integral derivative (P.I.D.) type controller. The slave controller 414 then computes equivalent motor currents for these joint torque values, and drives electrical motors on the slave 416 with these currents as indicated by arrow AB7. The slave 416 is then caused to be driven to the new slave position which corresponds to the new master position.

The control steps involved in the master/slave control system 400 as explained above are typically carried out at about 1300 cycles per second or faster. It will be appreciated that although reference is made to an initial position and new position of the master, these positions are typically incremental stages of a master control movement. Thus, the slave is continually tracking incremental new positions of the master.

The master/slave control system 400 also makes provision for force feedback. Thus, should the slave 416 (i.e., its end effector) be subjected to an environmental force at the surgical site, e.g., in the case where the end effector pushes against tissue, or the like, such a force is fed back to the master 404 so that the surgeon may feel it. Accordingly, when the slave 416 is tracking movement of the master 404 as described above and the slave 416 pushes against an object at the surgical site resulting in an equal pushing force against the slave 416, which urges the slave 416 to move to another position, similar steps as described above in the forward or control path take place in the feedback path.

The surgical environment is indicated at 418 in FIG. 4. In the case where an environmental force is applied on the slave 416, such a force causes displacement of the end effector. This displacement is sensed by the encoders on the slave 416 which generate signals that are input to the slave controller 414 as indicated by arrow BA2. The slave controller 414 computes a position in joint space corresponding to the encoder signals, and provides the position to the slave kinematics converter 412, as indicated by arrow BA3.

The slave kinematics converter 412 computes a Cartesian space position corresponding to the joint space position, and provides the Cartesian space position to the bilateral controller 410, as indicated by arrow BA4. The bilateral controller 410 compares the Cartesian space position of the slave with a Cartesian space position of the master to generate a positional deviation in Cartesian space, and computes a force value corresponding to that positional deviation that would be required to move the master 404 into a position in Cartesian space which corresponds with the slave position in Cartesian space. The force value is then provided to the master kinematics converter 408, as indicated by arrow BA5.

The master kinematics converter 408 calculates from the force value received from the bilateral controller 410, corresponding torque values for the joint motors of the master 404. This is typically performed by a Jacobian Transpose function in the master kinematics converter 408. The torque values are then provided to the master controller 406, as indicated by arrow BA6. The master controller 406, then determines master electric motor currents corresponding to the torque values, and drives the electric motors on the master 404 with these currents, as indicated by arrow BA7. The master 404 is thus caused to move to a position corresponding to the slave position.

Although the feedback has been described with respect to a new position to which the master 404 is being driven to track the slave 416, it is to be appreciated that the surgeon is gripping the master 404 so that the master 404 does not necessarily move. The surgeon however feels a force resulting from feedback torques on the master 404 which he counters because he is holding onto the master 404.

In performing collaborative minimally invasive surgical procedures or training in such procedures, it is useful at times for the lead or mentor surgeon to selectively associate certain master input devices with certain slave robotic mechanisms so that different surgeons may control different surgery-related devices in a collaborative effort or so that selected trainees may practice or experience a minimally invasive surgical procedure under the guidance or control of the mentor surgeon. Some examples of such selective master/slave associations are illustrated in FIGS. 5-9, wherein each master depicted therein includes the master manipulator 404 and master processing 420 of FIG. 4 and each slave depicted therein includes the slave manipulator 416 and slave processing 430 of FIG. 4.

Figure 5:
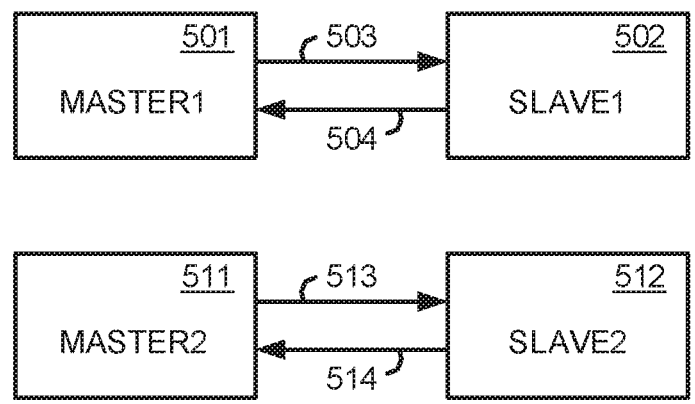
FIGS. 5-9 illustrate block diagrams of selected master/slave associations for a multi-user medical robotic system, utilizing aspects of the present invention.

In FIG. 5, an exclusive operation master/slave association is shown in which master 501 has exclusive control over slave 502 (and its attached surgery-related device), and master 511 has exclusive control over slave 512 (and its attached surgery-related device). In this configuration, the masters, 501 and 511, may be controlled by the right and left hands of a surgeon while performing a minimally invasive surgical procedure, or they may be controlled by different surgeons in a collaborative minimally invasive surgical procedure. The master/slave control system 400 may be used for each associated master/slave pair so that lines 503 and 513 (master to slave direction) correspond to its forward path AB4 line and lines 504 and 514 (slave to master direction) correspond to its feedback path BA5 line.

Figure 6:
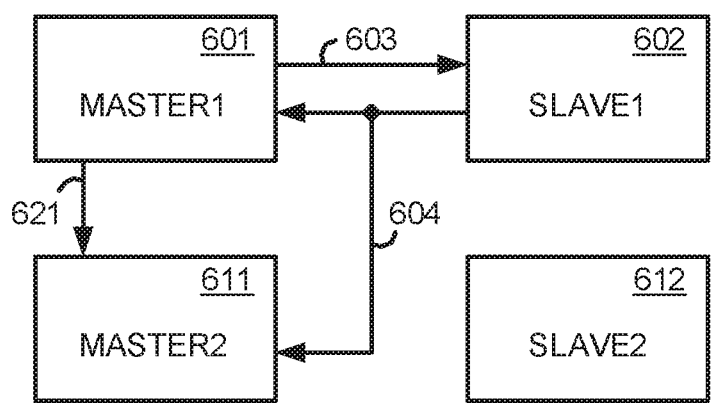

In FIG. 6, a unilateral control master/slave association is shown in which master 601 has exclusive control over slave 602 (and its attached surgery-related device), but input and reflected force (or position) values are provided to the master 611 as well as the master 601. In this configuration, although the master 611 cannot control the slave 602, it tracks the master 601 so that a surgeon holding the master input device of master 611 can feel and experience movement of the master input device of master 601 as it is being manipulated by another surgeon. Thus, this sort of configuration may be useful in training surgeons by allowing them to experience the movement of the master input device of the master 601 as it is being manipulated by a mentor surgeon during a minimally invasive surgical procedure, while viewing the surgical site in their respective displays and communicating with the mentor surgeon using their respective headsets.

Figure 7:
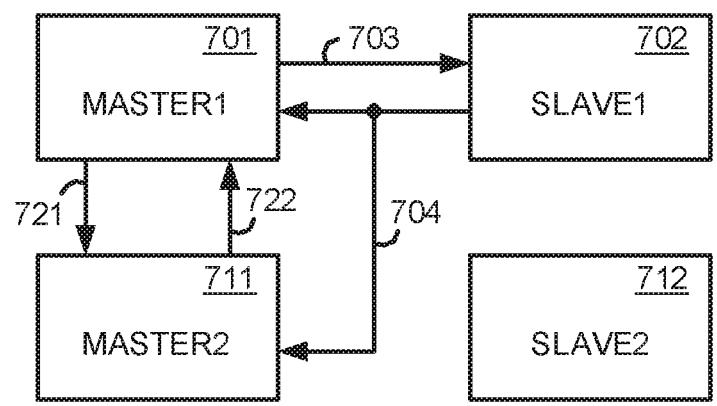

In FIG. 7, a modified version of the unilateral control master/slave association is shown. In this configuration, not only does the surgeon holding the master input device of master 711 experience the movement of (and forces exerted against) the master input device of the master 701 as it is being manipulated by another surgeon during a minimally invasive surgical procedure, the surgeon associated with master 711 can also "nudge" the master input device of the master 701 by manipulating his/her master input device since a force value corresponding to such nudging is provided back to the master 701, as indicated by the arrow 722. This "nudging" master/slave configuration is useful for training surgeons, because it allows a trainee surgeon to practice by performing the surgical procedure by manipulating the slave 702 (and its attached surgery-related device) using the master input device of his/her master 701, while the mentor surgeon monitors such manipulation by viewing the surgical site on his/her display while feeling the movement of the trainee surgeon's master input device through input and feedback forces, respectively indicated by arrows 721 and 704. If the mentor surgeon thinks that the trainee surgeon should modify his/her operation of his/her master input device, the mentor surgeon can nudge the trainee surgeon's master input device accordingly, while at the same time, communicating such recommendation verbally to the trainee surgeon using a shared audio system through their respective headsets.

Figure 8:
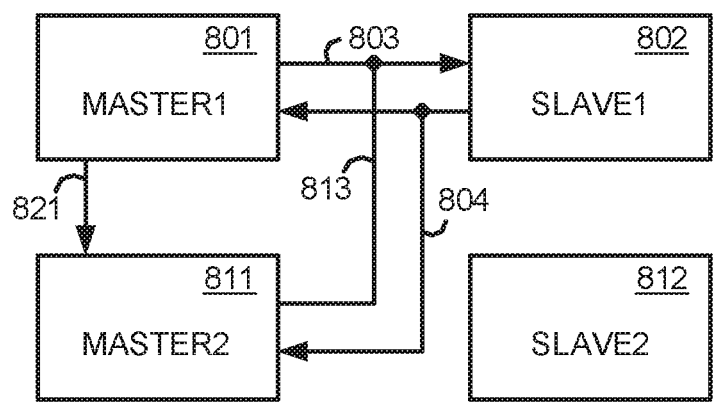

In FIG. 8, a unilateral, shared master/slave association, which is a variant of the nudging configuration of FIG. 7, is shown in which either (or both) masters 801 and 811 may control slave 802. In this configuration, not only does the surgeon holding the master input device of master 811 experience the movement of (and forces exerted against) the master input device of the master 801 as it is being manipulated by another surgeon during a minimally invasive surgical procedure, the surgeon associated with master 811 can also control the slave 802 if desired, as indicated by the arrow 813. This "override" master/slave configuration is useful for training surgeons, because it allows a trainee surgeon to practice by performing the surgical procedure by manipulating the slave 802 (and its attached surgery-related device) using the master input device of his/her master 801, while the mentor surgeon monitors such manipulation by viewing the surgical site on his/her display while feeling the movement of the trainee surgeon's master input device through input and feedback forces, respectively indicated by arrows 821 and 804. If the mentor surgeon finds it necessary to assume control of the slave 802 to avoid injury to a patient, the mentor surgeon can assert such control accordingly, while at the same time, communicating that he/she is taking over control verbally to the trainee surgeon through a shared audio system.

Figure 9:
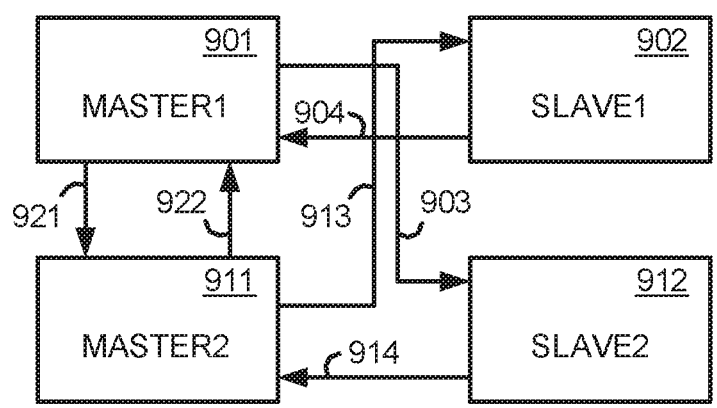

In FIG. 9, a bilateral master/slave association is shown in which masters, 901 and 912, and slaves, 902 and 912, all move in tandem, tracking each other's movements. In this configuration, the slave 912 (and its attached surgery-related device) may be controlled by a surgeon using the master 901, while another surgeon experiences its movement by loosely holding the master input device for the other master 911. The slave 902 in this case is generally non-operative in the sense that it is not directly participating in the minimally invasive surgical procedure. In particular, the slave 902 either may not have the distal end of its slave robotic mechanism inserted in the patient so that its robotic arm moves, but does not result in any action taking place in the surgical site, or the slave 902 may only include a computer model of the linkages, joints, and joint motors of its slave robotic mechanism, rather than the actual slave robotic mechanism.

However, the slave 902 does move in tandem with the slave 912 (in actuality or through simulation) as the surgeon manipulating the master input device of the master 901 causes the slave 912 to move, because a force (or position) value corresponding to such manipulation is provided to the master 911, as indicated by arrow 921, and the master 911 controls the slave 902 to move accordingly, as indicated by arrow 913. Any forces asserted against the surgery-related device attached to the distal end of the slave robotic mechanism of the slave 912 are then fed back to the master input device of the master 911, as indicated by the arrow 914.

Note that the surgeon associated with the master 911 can effectively "nudge" the master 901 by manipulating the master input device of the master 911. Therefore, the bilateral master/slave association shown in FIG. 9 can also be used in the training of surgeons in a similar manner as the "nudging" and unilateral, shared master/slave associations respectively shown in FIGS. 7 and 8.

Figure 10:
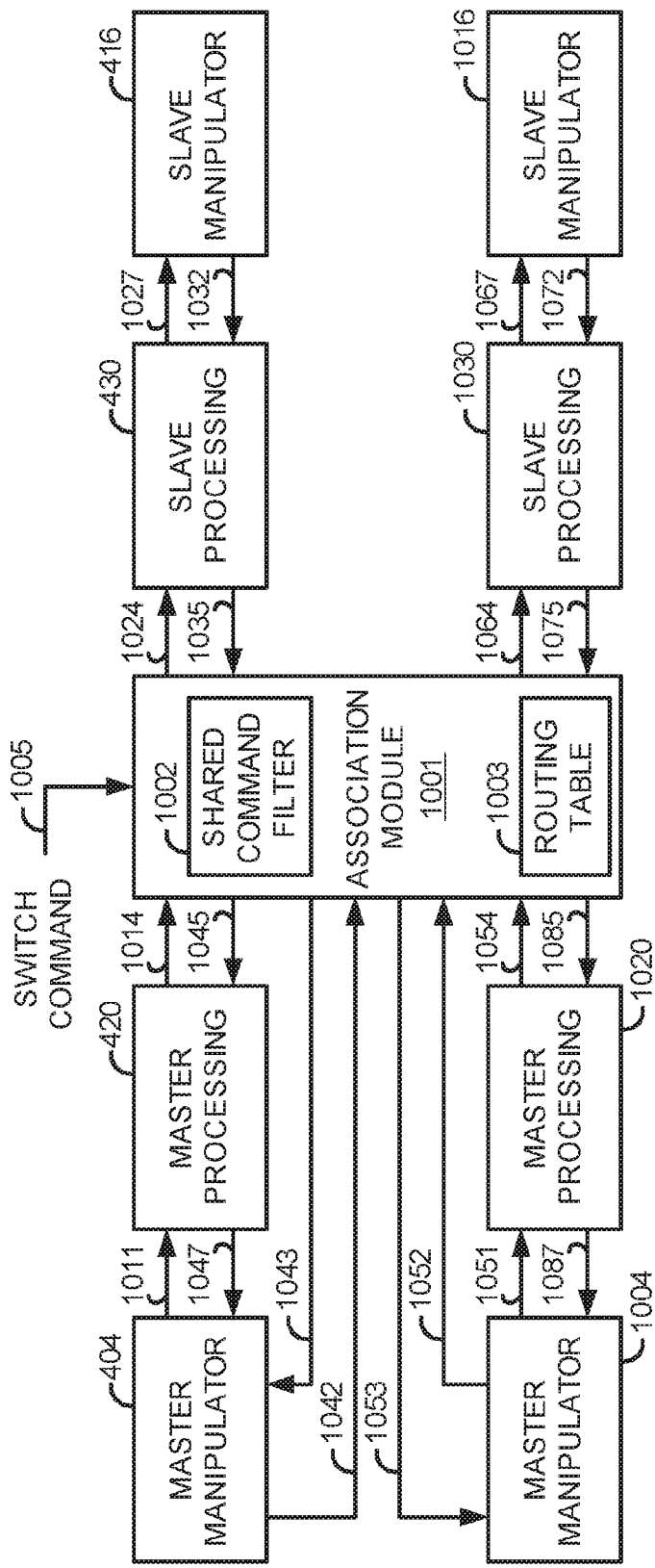
FIG. 10 illustrates a block diagram of components of the multi-user medical robotic system for selective association of masters and slaves, utilizing aspects of the present invention.

FIG. 10 illustrates a block diagram of components of the multi-user medical robotic system for selective association of master manipulators (also referred to as "master input devices"), 404 and 1004, with slave manipulators (also referred to as "slave robotic mechanisms"), 416 and 1016. Although only two master manipulators and two slave manipulators are shown in this example, it is to be appreciated that any number of master manipulators may be associated with any number of slave manipulators in the system, limited only by master control station port availability, memory capacity, and processing capability/requirements.

The master processing unit 420 includes the master controller 406 and the master kinematics converter 408 and generally operates as described in reference to FIG. 4, and the master processing unit 1020 is similarly configured and functionally equivalent to the master processing unit 420. The slave processing unit 430 includes the slave controller 414, slave kinematics converter 412, and the bilateral controller 410 and generally operates as described in reference to FIG. 4, and the slave processing unit 1030 is similarly configured and functionally equivalent to the slave processing unit 430.

An association module 1001 includes a shared command filter 1002 and a routing table 1003 for selectively associating master manipulators, 404 and 1004, with slave manipulators, 416 and 1016. In brief, the routing table 1003 indicates which inputs are routed to which outputs of the association module 1001, and the shared command filter 1002 determines how shared command of a slave manipulator by two master manipulators is handled. One or more switch commands 1005 are provided to the association module 1001 as a means for a user to alter parameters of the shared command filter 1002 or values in the routing table 1003 so as to change or switch the selected associations between master and slave manipulators. The current parameters of the shared command filter 1002 and/or values in the routing table 1003 may be indicated to the user using a plurality of icons on a graphical user interface of an auxiliary display or the user's master control station display, or they may be indicated by a plurality of light-emitting-diodes or other such indicators on or adjacent to the user's master control station, or they may be indicated by any other display mechanism.

The switch command(s) 1005 may be generated by any one or combination of: the user interacting with one or more buttons on the master input devices, the user interacting with one or more foot pedals associated with the user's master control station, the user providing recognizable voice commands to a voice recognition (i.e., word recognition) and processing system, the user interacting with one or more menus displayed on the user's master control station display, or the user interacting with any other conventional input mechanism of such sort.

In a preferred embodiment compatible with the multi-user medical robotic system of FIG. 1, master processing 420 is performed as executable program code on a processor associated with the master control station of the master manipulator 404, and master processing 1020 is also performed as executable program code on a processor associated with the master control station of the master manipulator 1004. Both master control stations in this case may be Trainee master control stations, such as master control stations 131 and 161 of FIG. 1, or one of the master control stations may be the Mentor master control station 101 and the other, a Trainee master control station.

The slave processing 430, the slave processing 1030, and the association module 1001 are preferably included as executable program or table code on the processor 220 associated with the Mentor master control station 101. The switch command(s) 1005 in this case originate from action taken by the Mentor Surgeon (M) operating the Mentor master control station 101.

The Mentor master control station 101 preferably performs the slave processing for all slave robotic mechanisms 121~123, because it communicates directly with the slave robotic mechanisms 121~123, whereas the Trainee master control stations only communicate indirectly with the slave robotic mechanisms 121~123 through the Mentor master control station 101. On the other hand, the Trainee master control stations preferably perform the master processing for their respective master input devices, so that such processing may be performed in parallel with the slave processing (while maintaining time synchronization) while off-loading these processing requirements from the processor of the Mentor master control station 101. Thus, this distribution of processing makes efficient use of processor resources and minimizes processing delay.

One feature of the present invention is the capability to selectively associate on-the-fly both command and feedback paths between the master and slave manipulators. For example, the exclusive operation master/slave association shown in FIG. 5 may be altered on-the-fly (i.e., during a minimally invasive surgical procedure rather than at set-up) to the bilateral master/slave association shown in FIG. 9 by re-associating the command path of the master 501 from the slave 502 to the slave 512 while maintaining the feedback path of the slave 502 to the master 501, re-associating the command path of the master 511 from the slave 512 to the slave 502 while maintaining the feedback path of the slave 512 to the master 511, providing a value indicating the input force applied against the master 501 to the master 511, and providing a value indicating the input force applied against the master 511 to the master 501.

Figure 11:
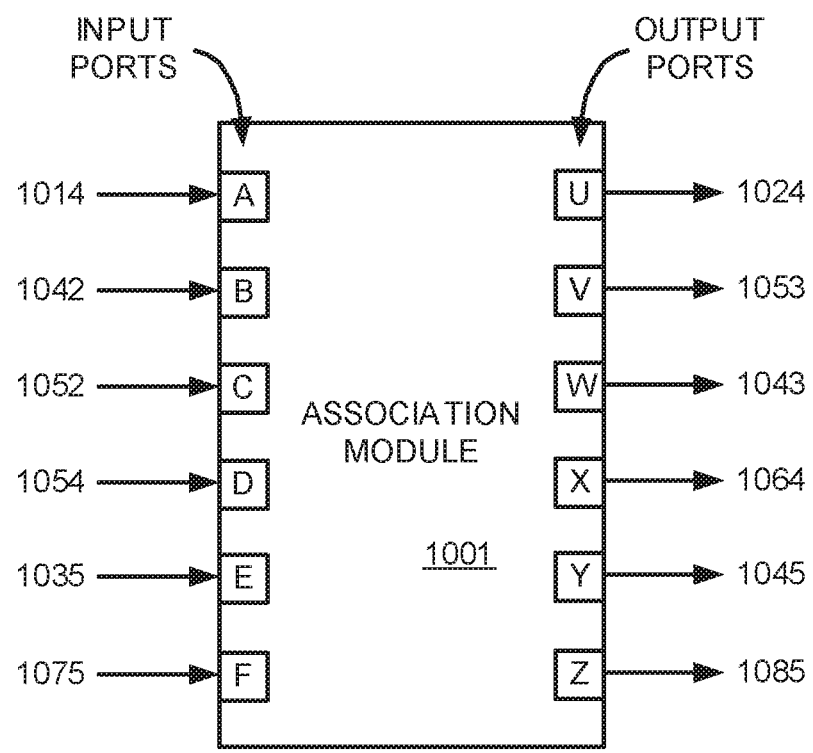
FIG. 11 illustrates an example of input/output ports for an association module, utilizing aspects of the present invention.

FIG. 11 illustrates an example of input/output ports for the association module 1001, in which input ports A~F are shown on the left side of the association module 1001 for convenience, and output ports U~Z are shown on the right side of the association module 1001 for convenience.

Input port A is assigned to the output of the master processing 420 which is provided on line 1014 of FIG. 10, input port B is assigned to the surgeon force input to the master manipulator 404 which is provided on line 1042 of FIG. 10, input port C is assigned to surgeon force input to the master manipulator 1004 which is provided on line 1052 of FIG. 10, input port D is assigned to the output of the master processing 1020 which is provided on line 1054 of FIG. 10, input port E is assigned to the output of the slave processing 430 which is provided on line 1035 of FIG. 10, and input port F is assigned to output of the slave processing 1030 which is provided on line 1075 of FIG. 10.

Output port U is assigned to the input to the slave processing 430 which is provided on line 1024 of FIG. 10, output port V is assigned to the input force to the master manipulator 1004 which is provided on line 1053 of FIG. 10, output port W is assigned to the input force to the master manipulator 404 which is provided on line 1042 of FIG. 10, output port X is assigned to the input to the slave processing 1030 which is provided on line 1064 of FIG. 10, output port Y is assigned to the feedback to the master processing 420 which is provided on line 1045 of FIG. 10, and output port Z is assigned to the feedback to the master processing 1020 which is provided on line 1085 of FIG. 10.

FIG. 12 illustrates a routing table corresponding to the master/slave association shown in FIG. 9, and FIG. 13 illustrates a routing table corresponding to the master/slave association shown in FIG. 8. Referring to FIG. 12, input port A is connected to output port X (i.e., line 1014 is coupled to line 1064 of FIG. 10, which corresponds to line 903 of FIG. 9), input port B is coupled to output port V (i.e., line 1042 is coupled to line 1053 of FIG. 10, which corresponds to line 921 of FIG. 9), input port C is connected to output port W (i.e., line 1052 is coupled to line 1043 of FIG. 10, which corresponds to line 922 in FIG. 9), input port D is connected to output port U (i.e., line 1054 is coupled to line 1024 of FIG. 10, which corresponds to line 913 in FIG. 9), input port E is connected to output port Y (i.e., line 1035 is coupled to line 1045 of FIG. 10, which corresponds to line 904 in FIG. 9), and input port F is connected to output port Z (i.e., line 1075 is coupled to line 1083 of FIG. 10, which corresponds to line 914 in FIG. 9).

If the Mentor Surgeon (M) is operating the master 901 and desires at this point to change the master/slave association from that of FIG. 9 to that of FIG. 8, he/she provides appropriate switch command(s) 1005 by, for example, depressing a button on his/her right-hand master input device corresponding to the master 901 so that the command output of the master 901 is provided to the slave 902 instead of the slave 912, and selecting menu entries on his/her display to stop providing commands to or receiving force feedback from the slave 912, to provide the force feedback from the slave 902 to the master 911 (as well as continuing to do so to the master 901), and stop providing the input force exerted on the master input device of the master 911 to the master 901. Alternatively, as previously described, these switches may be done using foot pedals, voice actuation, or any combination of buttons, foot pedals, voice, display menu, or other actuation devices controllable by the Mentor Surgeon (M).

FIG. 13 illustrates the routing table resulting from the above described switch command(s) 1005 that places the master/slave association into the configuration shown in FIG. 8. In this case, input port A is connected to output port U (i.e., line 1014 is coupled to line 1024 of FIG. 10, which corresponds to line 803 of FIG. 8), input port B is coupled to output port V (i.e., line 1042 is coupled to line 1053 of FIG. 10, which corresponds to line 821 of FIG. 8), input port C is not connected to any output port, input port D is connected to output port U (i.e., line 1054 is coupled to line 1024 of FIG. 10, which corresponds to line 813 in FIG. 8), input port E is connected to output ports Y and Z (i.e., line 1035 is coupled to line 1045 and 1085 of FIG. 10, which corresponds to line 804 in FIG. 8), and input port F is not connected to any output port.

Referring back to FIG. 8 now, it is noted that the slave 802 has two command inputs, one from the master 801 and another from the master 811. This causes a control contention issue which may be resolved by the shared command filter 1002 of the association module 1001 of FIG. 10.

Figure 14:
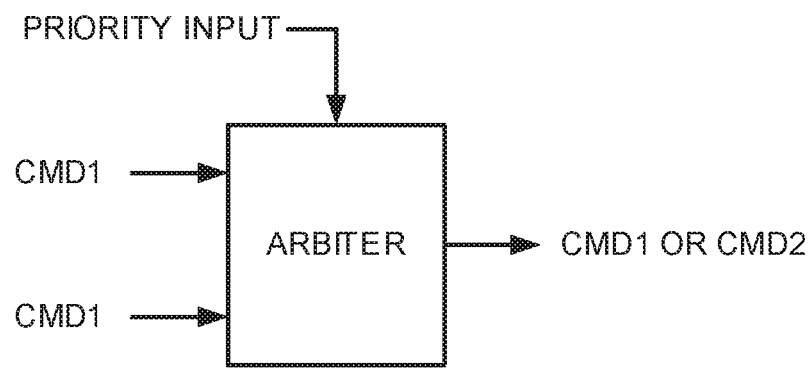
FIGS. 14 and 15 illustrate block diagrams for alternative embodiments of a shared command filter of an association module, utilizing aspects of the present invention.
Figure 15:
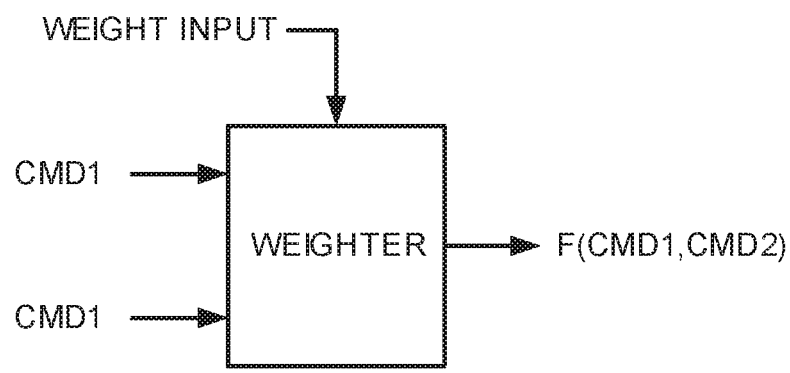

FIGS. 14 and 15 illustrate block diagrams for alternative embodiments of the shared command filter 1002. As shown in FIG. 14, the shared command filter 1002 takes the form of a simple arbiter, selecting either a first command input CMD1 or a second command input CMD2, depending upon a priority input which is provided as a switch command 1005 to the association module 1001 by the Mentor Surgeon (M) or programmed into or provided as a parameter value for its process code. As shown in FIG. 15, the shared command filter 1002 may also take the form of a weighter or weighting function that weights command inputs CMD1 and CMD2, and combines the weighted values to determine a shared command value to be provided to the slave. In this case, the respective weights of the first and second command inputs, CMD1 and CMD2, depend on a weight input which is provided as a switch command 1005 to the association module 1001 by the Mentor Surgeon (M), or programmed into or provided as parameter values for its process code.

In the foregoing description of the switching process from one master/slave association to another, it has been assumed that such switching occurs instantaneously. However, to avoid undesirable transient movement of the slave robotic mechanisms, it may be desirable in certain circumstances to phase-in the switching process (i.e., gradually reducing the strength of the signal being switched out while gradually increasing the strength of the signal being switched in), or using a clutch mechanism that disengages both signals and only engages the new signal, for example, after making sure that the position of the slave robotic mechanism being commanded by the new signal matches that of the old signal so that a sudden movement will not occur as a result of the change.

Although the various aspects of the present invention have been described with respect to a preferred embodiment, it will be understood that the invention is entitled to full protection within the full scope of the appended claims.

What is claimed is:
1. A medical system comprising:
a first slave manipulator configured to move a first device according to a first slave command;
a first input device operated by a first user, the first input device configured to generate a first command by the first user operating the first input device; and
a control station operated by a second user, the control station coupled to the first slave manipulator and the first input device, the control station including:
a second input device operated by the second user, the second input device configured to generate a second command by the second user operating the second input device;
means for generating one or more switch commands; and
an association module adapted to:
receive the first command and the second command,
generate the first slave command by using one or both of the first command and the second command according to the one or more switch commands; and
provide the first slave command to the first slave manipulator.
2. The medical system according to claim 1,
wherein the association module comprises:
a plurality of inputs, a first input associated with the first input device to receive the first command, a second input associated with the second input device to receive the second command;
a plurality of outputs, a first output associated with the first slave manipulator;
a routing table selectively coupling the plurality of inputs to the plurality of outputs according to the one or more switch commands; and
a shared command filter;
wherein the association module is configured to:
conditioned upon the routing table selectively coupling only one of the first command and the second command to the first output, generate the first slave command by using the selectively coupled one of the first command and the second command; and
conditioned upon the routing table selectively coupling both of the first command and the second command to the first output, coupling the first command and the second command to the shared command filter to generate the first slave command according to the one or more switch commands.
3. The medical system according to claim 2,
wherein the shared command filter comprises:
an arbiter configured to select one of the first command and the second command to be the first slave command, according to a priority input included among the one or more switch commands.
4. The medical system according to claim 2,
wherein the shared command filter comprises:
a weighting function configured to weight each of the first command and the second command to generate the first slave command, according to weight values, included among the one or more switch commands, for the first input device and the second input device.
5. The medical system according to claim 1,
wherein the means for generating one or more switch commands comprises:
means for phasing-in a new switch command and phasing-out an old switch command when selective coupling of the plurality of inputs to the plurality of outputs by the routing table is to change as a result of the old switch command being replaced with the new switch command.
6. The medical system according to claim 1,
wherein the means for generating one or more switch commands comprises any one or a combination of:
one or more buttons on the second input device, one or more foot pedals,
a voice recognition and processing system,
a graphical user interface, and
other user operable input mechanism.

* * * * *